US012559760B2

(12) United States Patent
Ghattyvenkatakrishna et al.

(10) Patent No.: US 12,559,760 B2
(45) Date of Patent: Feb. 24, 2026

(54) VECTORS AND EXPRESSION SYSTEMS FOR PRODUCING RECOMBINANT PROTEINS

(71) Applicant: AMGEN INC., Thousand Oaks, CA (US)

(72) Inventors: Pavan Ghattyvenkatakrishna, Thousand Oaks, CA (US); Hedieh Barkhordarian, Newbury Park, CA (US); Kristine Marie Daris, Thousand Oaks, CA (US); Charilyn Tejamo, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 1066 days.

(21) Appl. No.: 17/609,303

(22) PCT Filed: May 4, 2020

(86) PCT No.: PCT/US2020/031309
§ 371 (c)(1),
(2) Date: Nov. 5, 2021

(87) PCT Pub. No.: WO2020/227206
PCT Pub. Date: Nov. 12, 2020

(65) Prior Publication Data
US 2022/0243222 A1     Aug. 4, 2022

Related U.S. Application Data

(60) Provisional application No. 62/844,360, filed on May 7, 2019.

(51) Int. Cl.
| | |
|---|---|
| *C12N 15/64* | (2006.01) |
| *C07K 16/06* | (2006.01) |
| *C12N 5/16* | (2006.01) |
| *C12N 9/00* | (2006.01) |
| *C12N 9/12* | (2006.01) |
| *C12N 15/62* | (2006.01) |
| *C12N 15/85* | (2006.01) |

(52) U.S. Cl.
CPC ............. *C12N 15/64* (2013.01); *C07K 16/06* (2013.01); *C12N 5/16* (2013.01); *C12N 9/12* (2013.01); *C12N 9/93* (2013.01); *C12N 15/62* (2013.01); *C12N 15/85* (2013.01); *C12Y 603/02001* (2013.01); *C07K 2317/14* (2013.01); *C07K 2319/00* (2013.01); *C12N 9/00* (2013.01); *C12N 2840/203* (2013.01)

(58) Field of Classification Search
CPC ......... C12N 15/85; C12N 9/93; C12N 15/62; C12N 2840/203; C12N 15/52; C07K 16/06; C07K 2317/14; C07K 2319/00; C12Y 603/02001; C12Y 603/01002
USPC ........... 435/320.1, 183, 91.4; 530/387.1, 866
See application file for complete search history.

(56) References Cited

U.S. PATENT DOCUMENTS

| | | | |
|---|---|---|---|
| 5,624,818 A | 4/1997 | Eisenman et al. | |
| 5,916,771 A | 6/1999 | Hori et al. | |
| 2015/0337331 A1 | 11/2015 | Kakimoto et al. | |
| 2019/0127452 A1 * | 5/2019 | Ketchem ............ | C12N 15/1055 |

FOREIGN PATENT DOCUMENTS

| | | | | |
|---|---|---|---|---|
| WO | 1998/44350 A1 | 10/1998 | | |
| WO | 2003/35887 A1 | 5/2003 | | |
| WO | 2004/050879 A1 | 6/2004 | | |
| WO | 2008/119567 A2 | 10/2008 | | |
| WO | 2017/134140 A1 | 8/2017 | | |
| WO | WO-2017197098 A1 * | 11/2017 | ............ | C07K 16/00 |
| WO | 2018/162517 A1 | 9/2018 | | |

OTHER PUBLICATIONS

Lu & Feng 2008, Appl. Microbiol. Biotechnol., 79, 579-587. (Year: 2008).*
Ghosh et al. 2000. J. Am. Chem. Soc., 122, 5658-5659. (Year: 2000).*
Ishikawa et al. 2012, Protein Engineering, Design & Selection, 25(12), 813-820. (Year: 2012).*
Aldrich et al., EASE vectors for rapid stable expression of recombinant antibodies, Biotechnol. Prog, 19(5):1433-8 (2003).
Aldrich et al., Improved bicistronic mammalian expression vectors using expression augmenting sequence element (EASE), Cytotechnology, 28(1-3):9-17 (1998).
Altschul et al., Basic local alignment search tool, J. Mol. Biol., 215:403-410 (1990).
Altschul et al., Gapped BLAST and PSI-BLAST: a new generation of protein database search programs, Nucl. Acids Res., 25:3389-3402 (1997).
Bebbington et al., High-level expression of a recombinant antibody from myeloma cells using a glutamine synthetase gene as an amplifiable selectable marker, Biotechnology, 10(2):169-175 (1992).
Betz et al., Native-like and structurally characterized designed alpha-helical bundles, Curr. Opin. Struct. Biol., 5(4):457-463 (1995).
Bianchi et al., High-level expression of full-length antibodies using trans-complementing expression vectors, Biotechnol. Bioeng., 84(4):439-444 (2003).
Bird et al., Single-chain antigen-binding proteins, Science, 242:423-6 (1988).

(Continued)

*Primary Examiner* — Anne Marie S Wehbe
*Assistant Examiner* — Katie L Pennington
(74) *Attorney, Agent, or Firm* — MARSHALL, GERSTEIN & BORUN LLP

(57) ABSTRACT

Inventions disclosed herein relates to vectors and expression systems for producing heteromeric recombinant proteins such as monoclonal antibodies. Vectors and expression systems disclosed herein are based on the finding that the selectable marker glutamine synthetase can be divided into two fragments at selected amino acid positions of the glutamine synthetase polypeptide, and the two fragments can internet and/or associate to form a monomer and then a functional multimeric glutamine synthetase protein.

18 Claims, 4 Drawing Sheets

Specification includes a Sequence Listing.

(56)                    References Cited

OTHER PUBLICATIONS

Brinkmann et al., The making of bispecific antibodies, MABS, 9(2):182-212 (2017).

Chaudhary et al., A recombinant immunotoxin consisting of two antibody variable domains fused to Pseudomonas exotoxin, Nature, 339:394-397 (1989).

Colberre-Garapin et al., A new dominant hybrid selective marker for higher eukaryotic cells, J. Mol. Biol., 150(1):1-14 (1981).

Crick, The packing of a-helices: simple coiled-coils, Acta. Crystallogr., 6:689-697 (1953).

Curtis et al., Enhanced hematopoietic activity of a human granulocyte/macrophage colony-stimulating factor-interleukin 3 fusion protein, Proc. Natl. Acad. Sci., 88(13):5809-5813 (1991).

Ghosh et al., Antiparallel Leucine Zipper-Directed Protein Reassembly: Application to the Green Fluorescent Protein, J. Am. Chem. Soc., 122(23):5658-5659 (2000).

Harbury et al., A switch between two-, three-, and four-stranded coiled coils in GCN4 leucine zipper mutants, Science, 262:1401-7 (1993).

Holliger et al., "Diabodies": small bivalent and bispecific antibody fragments, Proc. Natl. Acad. Sci. USA, 90(14):6444-6448 (1993).

Holliger et al., Engineered antibody fragments and the rise of single domains, Nature Biotechnology, 23(9):1126-1136 (2005).

Hudson et al., High avidity scFv multimers; diabodies and triabodies, J. Immunol. Methods, 231(1-2):177-89 (1999).

International Application No. PCT/US20/31309, International Preliminary Report on Patentability, mailed Nov. 18, 2021.

International Application No. PCT/US20/31309, International Search Report and Written Opinion, mailed Aug. 4, 2020.

Ishikawa et al., Generation of a dual-functional split-reporter protein for monitoring membrane fusion using self-associating split GFP, Protein Eng. Des. Sel., 25(12):813-20 (2012).

Jang et al., Cap-independent translation of encephalomyocarditis virus RNA: structural elements of the internal ribosomal entry site and involvement of a cellular 57-KD RNA-binding protein, Genes & Dev., 4(9):1560-72 (1990).

Jang et al., Initiation of protein synthesis by internal entry of ribosomes into the 5' nontranslated region of encephalomyocarditis virus RNA in vivo, J. Virol., 63(4):1651-60 (1989).

Kaufman, Large Scale Mammalian Cell Culture, Marcel Dekker, New York, New York, USA, 15-69 (1990).

Kurokawa et al., Differential orientations of the DNA-binding domain and carboxy-terminal dimerization interface regulate binding site selection by nuclear receptor heterodimers, Genes. Dev., 7:1423-1435 (1993).

Larrick et al., Polymemse Chain Reaction Using Mixed Primers: Cloning of Human Monoclonal Antibody Variable Region Genes from Single Hybridoma Cells, Biotechnology, 7:934-938 (1989).

Lau et al., Synthesis of a model protein of defined secondary and quaternary structure. Effect of chain length on the stabilization and formation of two-stranded alpha-helical coiled-coils, J. Biol. Chem., 259(21):13253-13261 (1984).

Lowy et al., Isolation of transforming DNA: cloning the hamster aprt gene, Cell, 22(3):817-23 (1980).

Marmonstein et al., DNA recognition by GAL4: structure of a protein-DNA complex, Nature, 356:408-414 (1992).

Mitchell, The GLN1 locus of *Saccharomyces cerevisiae* encodes glutamine synthetase, Genetics, 111(2):243-258 (1985).

Monera et al., Electrostatic interactions control the parallel and antiparallel orientation of alpha-helical chains in two-stranded alpha-helical coiled-coils, Biochemistry, 33(13):3862-3871 (1994).

Mulligan et al., Selection for animal cells that express the *Escherichia coli* gene coding for xanthine-guanine phosphoribosyltransferase, Proc. Natl. Acad. Sci. USA, 78(4):2072-6 (1981).

Murre et al., Interactions between heterologous helix-loop-helix proteins generate complexes that bind specifically to a common DNA sequence, Cell, 58(3):537-544 (1989).

Needleman et al., A general method applicable to the search for similarities in the amino acid sequence of two proteins, J. Mol. Biol., 48:443-53 (1970).

Oakle et al., The design of antiparallel coiled coils, Curr. Opin. Struct. Biol., 11(4):450-457 (2001).

Pearson et al., Improved tools for biological sequence comparison, Proc. Nat. Acad. Sci. USA., 85:2444-8(1988).

Rasmussen et al., Isolation, characterization and recombinant protein expression in Veggie-CHO: A serum-free CHO host cell line, Cytotechnology, 28(1-3):31-42 (1998).

Reichmann et al., Reshaping human antibodies for therapy, Nature, 332:323-329 (1988).

Remy et al., Clonal selection and in vivo quantitation of protein interactions with protein-fragment complementation assays, Proc. Natl. Acad. Sci., 96(10):5394-5399 (1999).

Roberts et al., Generation of an antibody with enhanced affinity and specificity for its antigen by protein engineering, Nature, 328:731-734 (1987).

Sambrook et al., Molecular Cloning: A Laboratory Manual, 2nd Edition, Cold Spring Harbor, New York (1989).

Santerre et al., Expression of prokaryotic genes for hygromycin B and G418 resistance as dominant-selection markers in mouse L cells, Gene., 30(1-3):147-56 (1984).

Smith et al., Comparison of biosequences , Adv. Appl. Math., 2:482-89 (1981).

Szybalska et al., Genetics of human cell line. IV. DNA-mediated heritable transformation of a biochemical trait, Proc. Natl. Acad. Sci. USA, 48(12):2026-34 (1962).

Verhoeyen et al., Reshaping human antibodies: grafting an antilysozyme activity, Science, 239:1534-1536 (1988).

Wigler et al., Transfer of purified herpes virus thymidine kinase gene to cultured mouse cells, Cell, 11(1):223-32 (1977).

Zhang et al., Antibody-promoted dimerization bypasses the regulation of DNA binding by the heme domain of the yeast transcriptional activator HAP1, Proc. Natl. Acad. Sci. USA, 90(7):2851-2855 (1993).

* cited by examiner

Figure 1, cont.
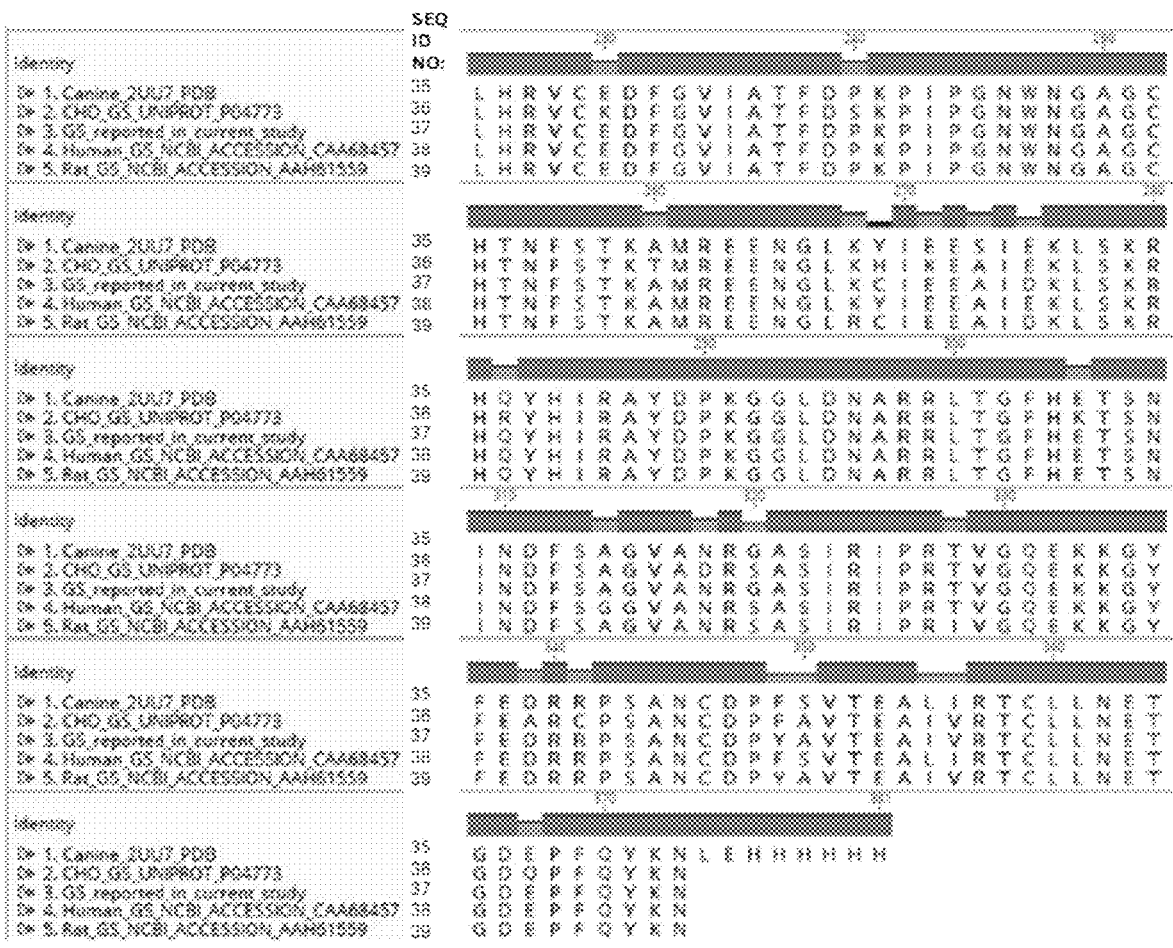

VECTORS AND EXPRESSION SYSTEMS FOR PRODUCING RECOMBINANT PROTEINS

CROSS REFERENCE TO RELATED APPLICATIONS

This application is a U.S. national stage under 35 U.S.C. § 371 of International Patent Application No. PCT/US2020/031309, filed May 4, 2020, which claims priority to U.S. Provisional Patent Application No. 62/844,360, filed May 7, 2019, the entire contents of each of which are fully incorporated herein by reference.

INCORPORATION BY REFERENCE OF MATERIAL SUBMITTED ELECTRONICALLY

A Sequence Listing, which is a part of the present disclosure, is submitted concurrently with the specification as a text file. The name of the text file containing the Sequence Listing is "57069_SubSeqListing.txt." The Sequence Listing was created on May 27, 2025, and is 126,745 bytes in size. The subject matter of the Sequence Listing is incorporated by reference herein in its entirety.

FIELD OF THE INVENTION

Inventions disclosed herein generally relate to the field of vectors and expression systems for producing recombinant proteins. Specifically, inventions disclosed herein relate to vectors, expression systems and methods for producing heteromeric protein complexes comprising different polypeptides.

BACKGROUND OF THE INVENTION

Therapeutic proteins such as antibodies are an important class of medicines serving patients. Typically, therapeutic proteins are produced in recombinant cells that have been adapted for long term growth in culture. Many times, multiple heterologous recombinant polypeptides (e.g., heavy chain and light chain of an antibody) are expressed in these cells that can form heteromeric complexes.

Production of such heteromeric complexes requires expression systems that concurrently express different polypeptides in appropriate amounts to allow proper association and assembling of the polypeptides to form heteromeric complexes. For example, in the expression of an antibody, the heavy chain and light chain of the antibody need to be expressed in roughly equal amounts for proper association of the heavy and light chains and the production of the antibody. However, a difficulty that may be encountered in antibody production is that either the heavy chain or the light chain is expressed to relatively high levels with respect to the corresponding partner, leading to improper and/or inefficient production of the antibody.

Different approaches have been used to address the difficulty. For instance, an expression system has been developed taking the advantage of reassociation of two fragments of the dihydrofolate reductase (DHFR) selectable maker to form an active molecule. See Bianchi A. and McGrew J., Biotechnol. Bioeng., 84 (4): 439-444 (2003). In that system, the expression of each antibody chain (heavy chain and light chain) is linked to the expression of a DHFR fragment, and survival in selective media that require expression of both DHFR fragments leads to the expression of roughly equal amounts of both chains.

Glutamine synthetase has been used as an amplifiable, selectable marker for high level expression of recombinant proteins. See e.g., Bebbington C. R. et al., BioTechnology, 10:169-175 (1992). Glutamine synthetase is a multimeric protein responsible for the biosynthesis of glutamine by catalyzing the condensation of ammonia and glutamate. When a gene encoding a functional glutamine synthetase is introduced in a cell lacking endogenous glutamine synthetase (e.g., a glutamine synthetase knock out mammalian cell), the cell can grow in a glutamine-free medium. There have been efforts in developing expression systems that utilize intragenic complementation of glutamine synthetase, wherein each antibody chain is linked to each of two mutant glutamine synthetases that can complement each other to form a functional glutamine synthetase such that roughly equal amounts of each chain are expressed. Intragenic complementation is a phenomenon that occurs when a multimeric protein is formed from subunits produced by different mutant alleles of a gene (e.g., mutations that mapped to the 5' end of the glutamine synthetase gene could complement those in the 3' end). See e.g., Mitchell, A. P. Genetics 111, 243-258 (1985).

Despite these progresses, there is a continued need for vectors, expression systems and methods that are robust and express heteromeric recombinant proteins to high levels.

SUMMARY OF THE INVENTION

Disclosed herein are vectors, expression systems and methods for producing heteromeric complexes comprising different polypeptides. Vectors and expression systems disclosed herein are based on the finding that the selectable marker glutamine synthetase can be divided into two fragments at selected amino acid positions of the glutamine synthetase polypeptide, and the two fragments can interact and/or associate to form a monomer and then a functional multimeric glutamine synthetase protein. Specifically, in the vectors and expression systems disclosed herein, the expression of each polypeptide of a heteromeric complex (e.g., heavy and light chain of an antibody) is linked to the expression of a glutamine synthetase fragment, and the expression of the heteromeric complex is accomplished by growing a recombinant cell comprising the vector or the expression system under conditions that require the expression of a functional glutamine synthetase. These vectors and expression systems are robust and express proteins to high levels. In addition, they reduce the time required to select for cells expressing high levels of proteins.

In certain embodiments, disclosed herein is a vector comprising a) a first nucleic acid encoding a first polypeptide, b) a second nucleic acid encoding a first fragment of glutamine synthetase, wherein the transcription of the first nucleic acid is operably linked to the transcription of the second nucleic acid, c) a third nucleic acid encoding a third polypeptide, the third polypeptide is capable of associating with the first polypeptide to form a heteromeric complex, and d) a fourth nucleic acid encoding a second fragment of glutamine synthetase, wherein the transcription of the third nucleic acid is operably linked to the transcription of the fourth nucleic acid, and wherein the first fragment and the second fragment of glutamine synthetase associate to provide a selectable activity, and wherein the vector is capable of being transfected into mammalian cells and improving selection of the transfected cells.

In certain embodiments, disclosed herein is an expression system comprising: a) a first vector comprising a first nucleic acid encoding a first polypeptide, wherein the transcription of the first nucleic acid is operably linked to the transcription of a second nucleic acid encoding a first fragment of glutamine synthetase, and b) a second vector comprising a third nucleic acid encoding a third polypeptide, wherein the transcription of the third nucleic acid is operably linked to the transcription of a fourth nucleic acid encoding a second fragment of glutamine synthetase, wherein the first polypeptide is capable of associating with the third polypeptide to form a heteromeric complex, wherein the first and second fragments of glutamine synthetase associate to provide a selectable activity, and wherein the expression system is capable of being transfected into mammalian cells and improving selection of the transfected cells.

In certain embodiments, the first fragment of glutamine synthetase is an N-terminal fragment of glutamine synthetase and the second fragment of glutamine synthetase is a C-terminal fragment of glutamine synthetase, or the first fragment of glutamine synthetase is a C-terminal fragment of glutamine synthetase and the second fragment of glutamine synthetase is an N-terminal fragment of glutamine synthetase.

In certain embodiments of the vector or the expression system disclosed herein, the glutamine synthetase comprising the amino acid sequence of SEQ ID NO: 1, and the first and second fragments of glutamine synthetase are generated by splitting the glutamine synthetase polypeptide at an amino acid position selected from K52, E55, D92, G187, G245, R262, K291, G302 and D311 of SEQ ID NO: 1. In certain embodiments, the first and second fragments of glutamine synthetase are generated by splitting the glutamine synthetase polypeptide at an amino acid position selected from K52, E55, D92, G187, and G245 of SEQ ID NO: 1, and in certain embodiments, the first and second fragments of glutamine synthetase are generated by splitting the glutamine synthetase polypeptide at the amino acid position D92 or G187 of SEQ ID NO: 1.

In certain embodiments of the vector or the expression system disclosed herein, a) the first glutamine synthetase fragment comprises amino acid residues 1 to 51 of SEQ ID NO: 1 and the second glutamine synthetase fragment comprises amino acid residues 52 to 373 of SEQ ID NO: 1; or b) the first glutamine synthetase fragment comprises amino acid residues 1 to 52 of SEQ ID NO: 1 and the second glutamine synthetase fragment comprises amino acid residues 53 to 373 of SEQ ID NO: 1; or c) the first glutamine synthetase fragment comprises amino acid residues 1 to 54 of SEQ ID NO: 1 and the second glutamine synthetase fragment comprises amino acid residues 55 to 373 of SEQ ID NO: 1; or d) the first glutamine synthetase fragment comprises amino acid residues 1 to 55 of SEQ ID NO: 1 and the second glutamine synthetase fragment comprises amino acid residues 56 to 373 of SEQ ID NO: 1; or e) the first glutamine synthetase fragment comprises amino acid residues 1 to 91 of SEQ ID NO: 1 and the second glutamine synthetase fragment comprises amino acid residues 92 to 373 of SEQ ID NO: 1; or f) the first glutamine synthetase fragment comprises amino acid residues 1 to 92 of SEQ ID NO: 1 and the second glutamine synthetase fragment comprises amino acid residues 93 to 373 of SEQ ID NO: 1; or g) the first glutamine synthetase fragment comprises amino acid residues 1 to 186 of SEQ ID NO: 1 and the second glutamine synthetase fragment comprises amino acid residues 187 to 373 of SEQ ID NO: 1; or h) the first glutamine synthetase fragment comprises amino acid residues 1 to 187 of SEQ ID NO: 1 and the second glutamine synthetase fragment comprises amino acid residues 188 to 373 of SEQ ID NO: 1; or i) the first glutamine synthetase fragment comprises amino acid residues 1 to 244 of SEQ ID NO: 1 and the second glutamine synthetase fragment comprises amino acid residues 245 to 373 of SEQ ID NO: 1; or j) the first glutamine synthetase fragment comprises amino acid residues 1 to 245 of SEQ ID NO: 1 and the second glutamine synthetase fragment comprises amino acid residues 246 to 373 of SEQ ID NO: 1; or k) the first glutamine synthetase fragment comprises amino acid residues 1 to 261 of SEQ ID NO: 1 and the second glutamine synthetase fragment comprises amino acid residues 262 to 373 of SEQ ID NO: 1; or l) the first glutamine synthetase fragment comprises amino acid residues 1 to 262 of SEQ ID NO: 1 and the second glutamine synthetase fragment comprises amino acid residues 263 to 373 of SEQ ID NO: 1; or m) the first glutamine synthetase fragment comprises amino acid residues 1 to 301 of SEQ ID NO: 1 and the second glutamine synthetase fragment comprises amino acid residues 302 to 373 of SEQ ID NO: 1; or n) the first glutamine synthetase fragment comprises amino acid residues 1 to 302 of SEQ ID NO: 1 and the second glutamine synthetase fragment comprises amino acid residues 303 to 373 of SEQ ID NO: 1; or o) the first glutamine synthetase fragment comprises amino acid residues 1 to 310 of SEQ ID NO: 1 and the second glutamine synthetase fragment comprises amino acid residues 311 to 373 of SEQ ID NO: 1; or p) the first glutamine synthetase fragment comprises amino acid residues 1 to 311 of SEQ ID NO: 1 and the second glutamine synthetase fragment comprises amino acid residues 312 to 373 of SEQ ID NO: 1.

In certain embodiments, the glutamine synthetase is a mammalian glutamine synthetase having an amino acid sequence different from SEQ ID NO:1, and the first and second fragments of glutamine synthetase are generated by splitting the mammalian glutamine synthetase polypeptide at an amino acid position equivalent to an amino acid position selected from K52, E55, D92, G187, G245, R262, K291, G302 and D311 of SEQ ID NO: 1 according to sequence alignment; in certain embodiments, the first and second fragments of glutamine synthetase are generated by splitting the mammalian glutamine synthetase polypeptide at an amino acid position equivalent to an amino acid position selected from K52, E55, D92, G187, and G245 of SEQ ID NO: 1 according to sequence alignment; in certain embodiments, the first and second fragments of glutamine synthetase are generated by splitting the mammalian glutamine synthetase polypeptide at an amino acid position equivalent to the amino acid position D92 or G187 of SEQ ID NO: 1 according to sequence alignment.

In certain embodiments, the heteromeric complex is an antibody or an antigen binding molecule. In certain embodiments, a) the first polypeptide is a heavy chain of an antibody or a fragment thereof and the third polypeptide is a light chain of an antibody or a fragment thereof; or b) the first polypeptide is a heavy chain of an antibody or a fragment thereof and the third polypeptide is a light chain of an antibody or a fragment thereof. In certain embodiments, a) the first nucleic acid encodes an antibody heavy chain or a fragment thereof and the third nucleic acid encodes an antibody light chain or a fragment thereof; or b) the first nucleic acid encodes an antibody light chain or a fragment thereof and the third nucleic acid encodes an antibody heavy chain or a fragment thereof.

In certain embodiments, the vector disclosed herein, or one or both vectors of the expression system disclosed herein further comprises an internal ribosomal entry site (IRES) and/or an expression augmenting sequence element (EASE). In certain embodiments, the IRES occurs at a site selected from: a) a site between the first nucleic acid and the second nucleic acid; b) a site between the third nucleic acid and the fourth nucleic acid, and c) at sites between both first and second, and third and fourth nucleic acids. In certain embodiments, the IRES comprises the sequence of GAT-GATAATACCCTCGAGATCCGTGCCATCATG (SEQ ID NO: 2).

In certain embodiments, each of the first and second fragment of glutamine synthetase further comprises an interaction domain. In certain embodiments, the interaction domain is a leucine zipper or an antiparallel leucine zipper polypeptide. In certain embodiments, the interaction domain is a leucine zipper polypeptide of GCN4, C/EBP, c-Fos, c-Jun, c-Myc or c-Max. In certain embodiments, the interaction domain is a leucine zipper polypeptide having the following sequence: ALKKELQANKKELAQLK-WELQALKKELAQ EQLEKKLQALEKKLAQLEW-KNQALEKKLAQ (SEQ ID NO: 3). In certain embodiments, each of the first and second interaction domains comprise the amino acid sequence of ALKKELQANKKELAQLKWELQALKKELAQ (SEQ ID NO: 4) or EQLEKKLQALEKKLAQLEW-KNQALEKKLAQ (SEQ ID NO: 5).

In certain embodiments, each of the first and second interaction domains further comprises a linker linking the first or second interaction domain to an interaction domain. In certain embodiments, the linker comprises a sequence selected from GGPGG (SEQ ID NO: 8), GPGGG (SEQ ID NO: 9), GGGGSGGGGGS (SEQ ID NO: 10), GGGGS (SEQ ID NO: 11) and GGGGSGGGGS (SEQ ID NO: 12).

In certain embodiments, a) the first interaction domain is fused to the N-terminal of the first glutamine synthetase fragment and has the amino acid sequence of EQLEKKLQALEKKLAQLEW-KNQALEKKLAQGGGGSGGGGS (SEQ ID NO: 6) and the second interaction domain is fused to the C-terminal of the second glutamine synthetase fragment and has the amino acid sequence of GGGGSGGGGSALKKELQANKKELAQLK-WELQALKKELAQ (SEQ ID NO: 7); or b) the first interaction domain is fused to the C-terminal of the first glutamine synthetase fragment and has the amino acid sequence of GGGGSGGGGSALKKELQANKKELAQLK-WELQALKKELAQ (SEQ ID NO: 7) and the second interaction domain is fused to the N-terminal of the second glutamine synthetase fragment and has the amino acid sequence of EQLEKKLQALEKKLAQLEW-KNQALEKKLAQGGGGSGGGGS (SEQ ID NO: 6).

In certain embodiments, the vector disclosed herein, or one or both vectors of the expression system disclosed herein further comprises a fifth nucleic acid encoding a selectable marker selected from Zeomycin, neomycin, puromycin, Blasticidin S, and GPT.

In certain embodiments, disclosed herein is a host cell comprising the vector or the expression system disclosed herein. In certain embodiments, the host cell is CHO, VERO, BHK, HeLa, Cos, MDCK, 293, 3T3, WI338, or NSO cells. In certain embodiments, the host cell is CHO cells. In certain embodiments, the host cell lacks endogenous glutamine synthetase.

In certain embodiments, disclosed herein is a method of producing an antibody heavy chain or a fragment thereof and an antibody light chain or a fragment thereof comprising culturing the host cell under conditions wherein the heteromeric complex is expressed by the host cell. In certain embodiments, the method further comprises isolating the heteromeric complex.

DETAILED DESCRIPTION

Figure 1:
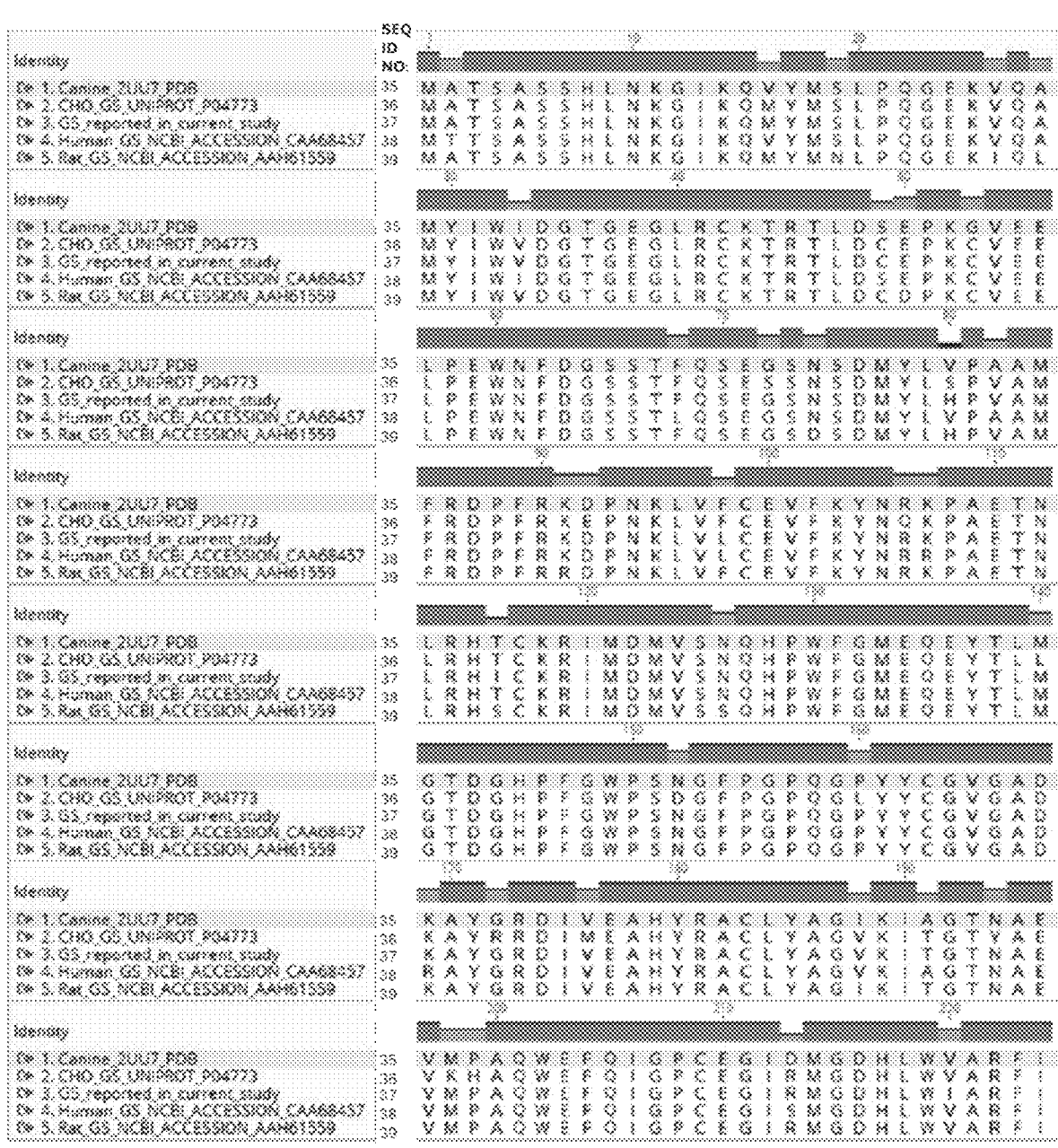
FIG. 1 shows sequence alignment of glutamine synthetase from different species using Geneious Aligner.

Disclosed herein are vectors, expression systems and methods for producing heteromeric complexes (e.g., monoclonal antibodies). The invention disclosed herein is advantageous in that they are robust, express each component of a heteromeric complex in proportion and to high levels. In addition, it reduces the time required to select for cells expressing high levels of proteins.

The invention disclosed herein utilizes that the selectable marker glutamine synthetase can be divided into two fragments at selected amino acid positions of the glutamine synthetase polypeptide, and the two fragments interact and form a functional glutamine synthetase protein when expressed together, thereby providing a selectable activity. The individual fragment does not have significant selectable activity when expressed alone, but they provide selectable activity when co-expressed. Polynucleotide encoding each glutamine synthetase fragment is operationally linked to a polynucleotide encoding a polypeptide that forms a heteromeric complex, and the expression of a functional glutamine synthetase in a selectable environment that requires the enzyme leads to the expression of the heteromeric complex.

Two fragments of glutamine synthetase generated at a splitting site may be expressed from one vector. Alternatively, two fragments of glutamine synthetase generated at a splitting site may be expressed from two vectors. Thus in some embodiments, disclosed herein is a vector comprising: a) a first nucleic acid encoding a first polypeptide, b) a second nucleic acid encoding a first fragment of glutamine synthetase, wherein the transcription of the first nucleic acid is operably linked to the transcription of the second nucleic acid, c) a third nucleic acid encoding a third polypeptide, the third polypeptide is capable of associating with the first polypeptide to form a heteromeric complex, and d) a fourth nucleic acid encoding a second fragment of glutamine synthetase, wherein the transcription of the third nucleic acid is operably linked to the transcription of the fourth nucleic acid, wherein the first fragment and the second fragment of glutamine synthetase associate to provide a selectable activity, and wherein the vector is capable of being transfected into mammalian cells and improving selection of the transfected cells.

In some embodiments, disclosed herein is an expression system comprising: a) a first vector comprising a first nucleic acid encoding a first polypeptide, wherein the transcription of the first nucleic acid is operably linked to the transcription of a second nucleic acid encoding a first fragment of glutamine synthetase, and b) a second vector comprising a third nucleic acid encoding a third polypeptide, wherein the transcription of the third nucleic acid is operably linked to the transcription of a fourth nucleic acid encoding a second fragment of glutamine synthetase, wherein the first polypeptide is capable of associating with the third polypeptide to form a heteromeric complex, the first and second fragments of glutamine synthetase associate to provide a selectable activity, and wherein the expression system is capable of being transfected into mammalian cells and improving selection of the transfected cells.

As used herein, the term "vector" is understood as expression vectors, which are DNA sequences that are required for transcription and translation of their DNAs in a eukaryotic host cell (e.g., a mammalian cell) after transfection with a vector. An appropriately constructed vector usually comprises at least one expressible marker selectable in eukaryotic cells (e.g., mammalian cells) and restriction sites for insertion of the expression cassette for the recombinant product gene under control of an upstream promoter region. Optionally, the vector can further comprise an internal ribosomal entry site (IRES) to facilitate translation. The vector may further comprise an origin of replication such as origin of Epstein Barr Virus (EBV) or SV40 virus for autonomous replication/episomal maintenance in eukaryotic host cells. Additional components may be added to facilitate replication in prokaryotic and/or eukaryotic cells, integration of the vector into a eukaryotic chromosome, and markers to aid in selection of and/or screening for cells containing the vector. Vectors include linear DNA fragments, DNA fragments encompassing nuclear targeting sequences or are specially optimized for interaction with transfection reagents, viruses, plasmids, phages, phagemids, cosmids, viruses, retroviruses and the like that can be shuttled and produced in bacteria.

As used herein, the term "host cell" is understood to include a cell that has been genetically engineered to express a polypeptide of interest. Genetically engineering a cell involves transfecting, transforming or transducing the cell with a nucleic acid encoding a recombinant polynucleotide molecule (a "gene of interest"), and/or otherwise altering (e.g., by homologous recombination and gene activation or fusion of a recombinant cell with a non-recombinant cell) so as to cause the host cell to express a desired recombinant polypeptide. Methods and vectors for genetically engineering cells and/or cell lines to express a polypeptide of interest are well known to those of skill in the art; for example, various techniques are illustrated in Current Protocols in Molecular Biology. Ausubel et al., eds. (Wiley & Sons, New York, 1988, and quarterly updates); Sambrook et al., Molecular Cloning: A Laboratory Manual (Cold Spring Laboratory Press, 1989); Kaufman, R. J., Large Scale Mammalian Cell Culture, 1990, pp. 15-69. The term includes the progeny of the parent cell, whether or not the progeny is identical in morphology or in genetic makeup to the original parent cell, so long as the gene of interest is present. A cell culture can comprise one or more host cells.

As used herein, the term "operably linked" refers to when one nucleic acid is placed into a functional relationship with another nucleic acid. More specifically, operably linked includes that two different nucleic acids encoding different polypeptides have transcription induced simultaneously. Operably linked is also intended to mean that the linked nucleic acids can be contiguous in a single transcriptional unit, while translation is directed from one or more ribosomal start sites (e.g., internal ribosomal start site).

As used herein, the term "heteromeric complex" is understood to include a molecular complex formed by the association of at least two different molecules. The association can be non-covalent interaction or covalent attachment, e.g., disulfide bonds. The two different molecules are typically two different polypeptides; however, the invention also contemplates heteromeric complexes between polypeptides and nucleic acids and between different nucleic acids. In some embodiments, the heteromeric complex provides a functional activity, such as, the ability to bind a substrate (e.g., an immunoglobulin capable of binding a corresponding antigen), enzymatic activity or the like. In some embodiments, the heteromeric complex is secreted into the culture medium of the host cell in which it is being produced.

In some embodiments, the heteromeric complex is an immunoglobulin molecule. The immunoglobulin in vertebrate systems is an antibody comprised of two identical light chains and two identical heavy chains. Each heavy and light chain has a variable region and a constant region. The four chains are joined together by disulfide bonds, such that each light chain is joined with a heavy chain and the heavy chains are connected across their tails forming a Y-shaped heteromeric complex. The amino-terminal portion of each chain includes a variable region of about 100 to 110 or more amino acids primarily responsible for antigen recognition. The carboxy-terminal portion of each chain defines a constant region primarily responsible for effector function. The heavy chain constant domain comprises three constant domains (CH1, CH2 and CH3) and a hinge region. Human light chains are classified as kappa and lambda light chains. Heavy chains are classified as mu, delta, gamma, alpha, or epsilon, and define the antibody's isotype as IgM, IgD, IgG, IgA, and IgE, respectively. Antibodies are well known in the art and may be from any origin, including human, non-human or a hybrid of both (e.g., human antibodies, humanized antibodies, chimeric antibodies, and antibodies from species other than human).

In some embodiments, the heteromeric complex is an antigen binding fragment of an antibody. Non-limiting examples of antigen binding fragments include Fab, Fab', (Fab')$_2$, and Fv. A Fab fragment is a monovalent fragment having the light chain variable domain (VL), heavy chain variable domain (VH), light chain constant domain (CL) and the first constant domain of the heavy chain (CH1); a F(ab')2 fragment is a bivalent fragment having two Fab' fragments linked by a disulfide bridge at the hinge region, and the F(ab') 2 fragment can be split into two Fab' fragments by mild reduction; an Fv fragment has the VL and VH domains of a single arm of an antibody. Antigen binding fragments of an antibody are well known and used in the art. Numerous techniques are known by which DNA encoding immunoglobulin molecules can be manipulated to yield DNAs capable of encoding recombinant proteins such as antibodies with enhanced affinity, or antigen binding fragment thereof. Sec, for example, Larrick et al. (1989), Biotechnology 7:934-938; Reichmann et al. (1988), Nature 332:323-327;

Roberts et al. (1987), Nature 328:731-734; Verhocyen et al. (1988), Science 239:1534-1536; Chaudhary et al. (1989), Nature 339:394-397.

In the vector or the expression system disclosed herein, the first nucleic acid encodes a first polypeptide, and the third nucleic acid encodes a third polypeptide, and the first and the third polypeptides are capable of associating with each other to form a heteromeric complex. In embodiments wherein the heteromeric complex is an antibody or an antigen binding fragment thereof, the heavy chain or a fragment thereof may be encoded by either the first or the third nucleic acid, and the light chain or a fragment thereof may be encoded by either the first or the third nucleic acid. Thus, in some embodiments, the first polypeptide is an immunoglobulin heavy chain or a fragment thereof and the third polypeptide is an immunoglobulin light chain or a fragment thereof. In some embodiments, the first polypeptide is an immunoglobulin light chain or a fragment thereof and the third polypeptide is an immunoglobulin heavy chain or a fragment thereof. When expressed using the vector or the expression system disclosed herein, the light chain or a fragment thereof is fused in frame to the first or the second glutamine synthetase fragment; while the heavy chain or a fragment thereof is fused in frame to the second or the first glutamine synthetase fragment.

In some embodiments, the heteromeric complex is a heterodimeric protein, e.g., a heterodimeric protein comprising two different polypeptides or hetero-oligomeric protein. In some embodiments, the heterodimeric protein is a bispecific antigen binding molecule. As used herein, the term "bispecific antigen binding molecule" is understood to include molecules that recognize two different epitopes either on the same antigen or on different antigens. Many bispecific antigen binding molecules known in the art are generated using recombinant DNA technology. See e.g., Holliger P. and Hudson P. J., Nature Biotech., 23 (9): 1126-1136 (2005); Brinkmann U. and Kontermann R. E., MABS, 9 (2): 182-212 (2017); Bird R, et al. Science, 242:423-6 (1988); Hudson P, Kortt A., J Immunol Methods. 231:177-89 (1999); Holliger P, et al., Proc Natl Acad Sci USA. 90:6444-8 (1993). Any bispecific antigen binding molecule can be made using the invention disclosed herein so long as the bispecific antigen binding molecule is comprised of two different polypeptides. In certain bispecific antigen binding molecules, the two different polypeptides may be linked covalently, e.g., by a short peptide linker, or non-covalently. Non-limiting examples of bispecific antigen binding molecules include bispecific scFv (diabody) molecules, bispecific sc(Fab)$_2$ molecules, bispecific Fab fusion molecules, bispecific scFv-Fc molecules, bispecific Fab-dsFv molecules, bispecific Fab-VHH molecules (see e.g., Brinkmann U. and Kontermann R. E., MABS, 9 (2): 182-212 (2017), the description of the various bispecific antigen binding molecules is incorporated herein by reference), and bispecific X-body molecules (see WO2017/134140).

Additional non-limiting examples of heterodimeric or hetero-oligomeric proteins include BMP2/BMP7, osteogenic protein, interleukin 1 converting enzyme (ICE), various interleukin receptors (e.g., the IL-18 receptor, IL-13 receptor, IL-4 receptor and IL-7 receptor), receptors of the nucleus such as retinoid receptors, T-cell receptors, integrins such as cell adhesion molecules, betal-integrins, tumor necrosis factor receptor and soluble and membrane bound forms of class I and class II major histocompatibility complex proteins (MHC). For heteromeric complexes that are receptors, the invention encompasses both soluble and membrane bound forms of the polypeptides. Descriptions of additional heteromeric proteins that can be produced according to the invention can be found in, for example, Human Cytokines: Handbook for Basic and Clinical Research, Vol. II (Aggarwal and Gutterman, eds. Blackwell Sciences, Cambridge Mass., 1998); Growth Factors: A Practical Approach (McKay and Leigh, Eds. Oxford University Press Inc., New York, 1993) and The Cytokine Handbook (A W Thompson, ed.; Academic Press, San Diego Calif.; 1991).

In embodiments wherein the heteromeric complex is a heterodimeric protein (e.g., bispecific scFv, bispecific sc (Fab) 2 or interleukin receptors), each polypeptide that forms the heterodimeric protein may be encoded by either the first or the third nucleic acid, and each is fused in frame to a first or a second glutamine synthetase fragment when expressed using the vector or the expression system.

Not wishing to be bound by any theory, it is believed that by using two glutamine synthetase fragments generated at a split site, the vector and expression system disclosed herein provide a more stringent selection condition and a robust expression of recombinant proteins. In addition to expressing heteromeric complexes, the vector and expression system disclosed herein are also useful for expressing proteins comprised of identical polypeptide, e.g., proteins comprised of homodimers and proteins comprised of the same polypeptide. Such proteins are known and used in the art, including, e.g., fusion proteins such as etanercept, afibercept, epoetin alfa, darbepoetin alfa, filgrastim, pegfilgrastim and BiTE® molecules (e.g., disclosed in WO2008/119567 and WO2017/134140, the structure and sequence of which are incorporated by reference). Thus, in certain embodiments, the first and third nucleic acid are identical, and/or the first and third nucleic acid encode the same polypeptide, and/or the first and third polypeptides are identical. In such embodiments, a protein is expressed when the first and third polypeptide are expressed by the vector or the expression system, or for a homodimeric protein, the protein is expressed when the first and third polypeptide are expressed by the vector or expression system and associate to form a homodimer.

Glutamine synthetase is an enzyme that catalyzes the synthesis of glutamine from glutamate and ammonia. It is a multimeric protein that can be composed of 8, 10, or 12 identical subunits stacked into two face-to-face rings. Glutamine synthetase from mouse and several other eukaryotic species were analyzed carefully to identify amino acid positions at which to split the polypeptide into a first and a second glutamine synthetase fragment that can interact/associate to form a functional multimeric glutamine synthetase protein when the two fragments are co-expressed. In the vector or the expression system disclosed herein, the first fragment of glutamine synthetase can be either an N-terminal portion or a C-terminal portion of glutamine synthetase. Similarly, the second fragment of glutamine synthetase can be either an N-terminal portion or a C-terminal portion of glutamine synthetase. In some embodiments, the first fragment of glutamine synthetase is an N-terminal fragment of glutamine synthetase and the second fragment of glutamine synthetase is a C-terminal fragment of glutamine synthetase. In some embodiments, the first fragment of glutamine synthetase is a C-terminal fragment of glutamine synthetase and the second fragment of glutamine synthetase is an N-terminal fragment of glutamine synthetase.

Any glutamine synthetase may be used in the invention disclosed herein so long as that, when co-expressed in a host cell (e.g., a mammalian cell), the first and second fragments of the glutamine synthetase interact/associate to form a monomer and then a functional enzyme to provide a selectable activity. In some embodiments, the glutamine synthetase is a mammalian glutamine synthetase. In some embodiment, the glutamine synthetase is a murine glutamine synthetase. In some embodiments, the glutamine synthetase is a mouse glutamine synthetase. In some embodiments, the glutamine synthetase is a non-mouse, mammalian glutamine synthetase. In some embodiments, the glutamine synthetase is a non-mouse, murine glutamine synthetase. In some embodiments, the glutamine synthetase comprises the amino acid sequence of SEQ ID NO: 1. In some embodiments, the glutamine synthetase is a mammalian glutamine synthetase having an amino acid sequence different from SEQ ID NO:1.

```
                                    (SEQ ID NO: 1)
    1  MATSASSHLNKGIKQMYMSLPQGEKVQAMYIWVDGTGEGLRC

KTRTLDCE

51  PKCVEELPEWNFDGSSTFQSEGSNSDMYLHPVAMFRDPFRKD

PNKLVLCE

101  VFKYNRKP AETNLRHICKRIMDMVSNQHPWFGMEQEYTLMG

TDGHPFGWP

151  SNGFPGPQGPYYCGVGADKAYGRDIVEAHYRACLYAGVKITG

TNAEVMPA

201  QWEFQIGPCEGIRMGDHLWI ARFILHRVCEDFGVI ATFDP

KPIPGNWNGA

251  GCHTNFSTKAMREENGLKCIEEAIDKLSKRHQYHIRAYDPKG

GLDNARRL

301  TGFHETSNINDFSAGVANRGASIRIPRTVGQEKKGYFEDRRP

SANCDPYA

351  VTEAIVRTCLLNETGDEPFQYKN*
```

In some embodiments, the glutamine synthetase comprises the amino acid sequence of SEQ ID NO:1. In some embodiments, the first and second fragments of glutamine synthetase are generated by splitting the glutamine synthetase polypeptide at an amino acid position selected from K52, E55, D92, G187, G245, R262, K291, G302 or D311 of SEQ ID NO: 1. In some embodiments, the first and second fragments of glutamine synthetase are generated by splitting the glutamine synthetase polypeptide at an amino acid position selected from K52, E55, D92, G187, or G245 of SEQ ID NO:1. In some embodiments, the first and second fragments of glutamine synthetase are generated by splitting the glutamine synthetase at the amino acid position D92 or G187 of SEQ ID NO:1.

In some embodiments, the glutamine synthetase is a non-mouse, mammalian glutamine synthetase or a mammalian glutamine synthetase having an amino acid sequence that is not identical to SEQ ID NO:1. Non-limiting examples of such glutamine synthetase include rat glutamine synthetase, hamster glutamine synthetase, canine glutamine synthetase, and human glutamine synthetase. Mammalian glutamine synthetases are conserved proteins, however, proteins from different species may contain some variations in amino acid sequence and/or number of amino acids. See e.g., FIG. 1. When a mammalian glutamine synthetase having an amino acid sequence that is not identical to SEQ ID NO: 1 is used, in some embodiments, the first and second fragments of glutamine synthetase are generated by splitting the mammalian glutamine synthetase polypeptide having an amino acid sequence different from SEQ ID NO: 1 at an amino acid position equivalent to an amino acid position selected from K52, E55, D92, G187, G245, R262, K291, G302 and D311 of SEQ ID NO: 1 according to sequence alignment; in some embodiments, the first and second fragments of glutamine synthetase are generated by splitting the mammalian glutamine synthetase polypeptide having an amino acid sequence different from SEQ ID NO:1 at an amino acid position equivalent to an amino acid position selected from K52, E55, D92, G187, and G245 of SEQ ID NO: 1 according to sequence alignment; in some embodiments, the first and second fragments of glutamine synthetase are generated by splitting the mammalian glutamine synthetase polypeptide having an amino acid sequence different from SEQ ID NO:1 at an amino acid position equivalent to the amino acid position D92 or G187 of SEQ ID NO: 1 according to sequence alignment.

Whether an amino acid position of a glutamine synthetase from a given species or whether an amino acid position of a glutamine synthetase having an amino acid sequence different from SEQ ID NO: 1 is equivalent to a specific amino acid position of SEQ ID NO: 1 can be determined by aligning that glutamine synthetase amino acid sequence and SEQ ID NO: 1. When aligning two sequences, typically one sequence serves as a reference sequence, to which a test sequence is compared. When comparing an amino acid sequence of a particular glutamine synthetase amino acid sequence and SEQ ID NO:1, SEQ ID NO:1 may be the reference sequence while a glutamine synthetase having an amino acid sequence different from SEQ ID NO: 1 is the test sequence.

Methods of alignment of sequences for comparison are well-known in the art. Optimal alignment of sequences for comparison can be conducted, e.g., by manual alignment and visual inspection, see, e.g., Current Protocols in Molecular Biology (Ausubel et al., eds. 1995 supplement); by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), or by computerized implementations of these algorithms (e.g., GAP, BESTFIT, FASTA, and TFASTA in the Wisconsin Genetics Software Package, Genetics Computer Group, 575 Science Dr., Madison, Wis.), ALIGN, or by ALIGN-2 (Genentech, South San Francisco, Calif.), Megalign (DNASTAR), or the Geneious Aligner or ClustalW (Available from Biomatters, www.geneious.com/), Clustal Omega or T-Coffee (available from European Molecular Biology Laboratory-European Bioinformatic Institute, www.cbi.ac.uk/Tools/msa/tcoffee/)).

A useful example of algorithm that is suitable for sequence alignment and determining percent sequence identity and sequence similarity is the BLAST and BLAST 2.0 algorithms, which are described in Altschul et al., Nuc. Acids Res. 25:3389-3402 (1977) and Altschul et al., J. Mol. Biol. 215:403-410 (1990), respectively. Software for performing BLAST analyses is publicly available through the National Center for Biotechnology Information (website at www.ncbi.nlm.nih.gov/). Other examples of software programs that are suitable for multiple sequence alignment and determining percent sequence identity and sequence similarity include Geneious Aligner, ClustalW, Clustal Omega, and T-coffee. Any of these software programs may be used for sequence alignment in the invention disclosed herein. In certain embodiments, Geneious Aligner or ClustalW is use for sequence alignment in the invention disclosed herein.

There are two different ways for splitting a glutamine synthetase polypeptide to generate a first and a second fragments of glutamine synthetase at an amino acid position. For example, splitting glutamine synthetase at amino acid position K52 of SEQ ID NO: 1 can be done such that the first glutamine synthetase fragment comprises amino acid residues 1 to 51 of SEQ ID NO: 1 and the second glutamine synthetase fragment comprises amino acid residues 52 to 373 of SEQ ID NO: 1, or the first glutamine synthetase fragment comprises amino acid residues 1 to 52 of SEQ ID NO: 1 and the second glutamine synthetase fragment comprises amino acid residues 53 to 373 of SEQ ID NO: 1. In the invention disclosed herein, splitting a glutamine syn- thetase polypeptide at an amino acid position include both ways of splitting the polypeptide.

Thus, when SEQ ID NO:1 is split at amino acid position E55, the first glutamine synthetase fragment can comprise amino acid residues 1 to 54 of SEQ ID NO: 1 and the second glutamine synthetase fragment can comprise amino acid residues 55 to 373 of SEQ ID NO: 1; or the first glutamine synthetase fragment can comprise amino acid residues 1 to 55 of SEQ ID NO: 1 and the second glutamine synthetase fragment can comprise amino acid residues 56 to 373 of SEQ ID NO: 1;

when SEQ ID NO:1 is split at amino acid position D92, the first glutamine synthetase fragment can comprise amino acid residues 1 to 91 of SEQ ID NO: 1 and the second glutamine synthetase fragment can comprise amino acid residues 92 to 373 of SEQ ID NO: 1; or the first glutamine synthetase fragment can comprise amino acid residues 1 to 92 of SEQ ID NO: 1 and the second glutamine synthetase fragment can comprise amino acid residues 93 to 373 of SEQ ID NO: 1;

when SEQ ID NO: 1 is split at amino acid position G187, the first glutamine synthetase fragment can comprise amino acid residues 1 to 186 of SEQ ID NO: 1 and the second glutamine synthetase fragment can comprise amino acid residues 187 to 373 of SEQ ID NO: 1; or the first glutamine synthetase fragment can comprise amino acid residues 1 to 187 of SEQ ID NO: 1 and the second glutamine synthetase fragment can comprise amino acid residues 188 to 373 of SEQ ID NO: 1;

when SEQ ID NO: 1 is split at amino acid position G245, the first glutamine synthetase fragment can comprise amino acid residues 1 to 244 of SEQ ID NO: 1 and the second glutamine synthetase fragment can comprise amino acid residues 245 to 373 of SEQ ID NO: 1; or the first glutamine synthetase fragment can comprise amino acid residues 1 to 245 of SEQ ID NO: 1 and the second glutamine synthetase fragment can comprise amino acid residues 246 to 373 of SEQ ID NO: 1;

when SEQ ID NO: 1 is split at amino acid position R262, the first glutamine synthetase fragment can comprise amino acid residues 1 to 261 of SEQ ID NO: 1 and the second glutamine synthetase fragment can comprise amino acid residues 262 to 373 of SEQ ID NO: 1; or the first glutamine synthetase fragment can comprise amino acid residues 1 to 262 of SEQ ID NO: 1 and the second glutamine synthetase fragment can comprise amino acid residues 263 to 373 of SEQ ID NO: 1;

when SEQ ID NO: 1 is split at amino acid position K291, the first glutamine synthetase fragment can comprise amino acid residues 1 to 290 of SEQ ID NO: 1 and the second glutamine synthetase fragment can comprise amino acid residues 291 to 373 of SEQ ID NO: 1; or the first glutamine synthetase fragment can comprise amino acid residues 1 to 291 of SEQ ID NO: 1 and the second glutamine synthetase fragment can comprise amino acid residues 292 to 373 of SEQ ID NO: 1;

when SEQ ID NO: 1 is split at amino acid position G302, the first glutamine synthetase fragment can comprise amino acid residues 1 to 301 of SEQ ID NO: 1 and the second glutamine synthetase fragment can comprise amino acid residues 302 to 373 of SEQ ID NO: 1; or the first glutamine synthetase fragment can comprise amino acid residues 1 to 302 of SEQ ID NO: 1 and the second glutamine synthetase fragment can comprise amino acid residues 303 to 373 of SEQ ID NO: 1;

when SEQ ID NO: 1 is split at amino acid position D311, the first glutamine synthetase fragment can comprise amino acid residues 1 to 310 of SEQ ID NO: 1 and the second glutamine synthetase fragment can comprise amino acid residues 311 to 373 of SEQ ID NO: 1; or the first glutamine synthetase fragment can comprise amino acid residues 1 to 311 of SEQ ID NO: 1 and the second glutamine synthetase fragment can comprise amino acid residues 312 to 373 of SEQ ID NO: 1.

The first or second glutamine synthetase fragment does not have significant selectable activity when expressed alone, but they interact/associate to form a monomer and then a functional glutamine synthetase when co-expressed. The optimal activity of the glutamine synthetase can depend upon their interaction and association, and as such can be facilitated by interaction domains. Such interaction domains can be endogenous or heterologous to the first and second glutamine synthetase fragment.

In some embodiments, each of the first and second fragment of glutamine synthetase may be expressed as a fusion protein to an interaction domain. This can be achieved by, e.g., fusing the nucleic acid encoding each of the first and second fragment of glutamine synthetase in frame with a nucleic acid encoding an interaction domain. An interaction domain can be either N-terminal or C-termi- nal to the first or the second domain. When expressed, the interaction domain promotes interaction/association of the two fragments thereby allowing the formation of a func- tional glutamine synthetase and providing a selectable activ- ity.

As used herein, an "interaction domain" is understood to include a domain (e.g., a polypeptide) capable of facilitating the interaction or association of two or more polypeptides. In some embodiments, the interaction domain is a dimeriza- tion domain. A dimerization domain can be a polypeptide capable of inducing interaction or association of two poly- peptides. There are two types of dimers, those capable of forming homodimers (with the same sequence), or heterodi- mers (with another sequence).

In some embodiments, the interaction domain is a leucine zipper coiled coil polypeptide. A leucine zipper typically comprises about 35 amino acids containing a characteristic seven residue repeat with hydrophobic residues at the first and fourth residues of the repeat. Harbury et al., Science 262: 1401 (1993). The two-stranded coiled-coil motif is characterized by two amphipathic $\alpha$-helical chains wrapping around each other into a left-handed superhelix. Crick, F. H. C., Acta Crystallogr. 6, 689-69 (1953). Although there are two possible orientations of the $\alpha$-helical chains to form a coiled-coil, parallel or antiparallel, a particular coiled-coil exists only in one specific orientation. See e.g., Monera, O. D., Kay, C. M., and Hodges, R. S. Biochemistry 33, 3862- 3871 (1994). A leucine zipper is amenable to fusion to a polypeptide for oligomerizing the polypeptide as it is relatively small and is less likely to disrupt the polypeptide's normal function than would be a larger interaction domain.

In some embodiments, the interaction domain is a parallel leucine zipper. Parallel leucine zippers include those naturally exist as well as those designed and synthesized de novo based on the study of naturally occurring parallel coiled coils. See e.g., Lau S Y M et al., J Biol Chem 259:13253-13261 (1984); Betz S F et al., Curr Opin Struct Biol, 5:457-463 (1995). In some embodiments, the interaction domain is an anti-parallel leucine zipper. Anti-parallel leucine zippers include those naturally exist as well as those designed and synthesized de novo based on the study of naturally occurring anti-parallel coiled coils. See e.g., Oakley, M. G., and Hollenbeck, J. J. Curr Opin Struct Biol 11, 450-457 (2001); Ghosh, Hamilton and Regan, JACS 122, 5658-5659 (2000).

In some embodiments, the interaction domain is selected from a leucine zipper domain of GCN4, C/EBP, c-Fos, c-Jun, c-Myc and c-Max. In some preferred embodiments, the interaction domain comprises the sequence of ALKKELQANKKELAQLKWELQALKKELAQ EQLEKKLQALEKKLAQLEWKNQALEKKLAQ (SEQ ID NO: 3). Typically, when used in the inventions disclosed herein, ALKKELQANKKELAQLKWELQALKKELAQ (SEQ ID NO: 4) is fused in frame to the C-terminal of a glutamine synthetase fragment, while EQLEKKLQALEKKLAQLEWKNQALEKKLAQ (SEQ ID NO: 5) is fused in frame to the N-terminal of another glutamine synthetase fragment.

In some embodiments, the interaction domain is a dimerization domain such as a helix-loop-helix dimerization domain. Non-limiting examples of helix-loop-helix dimerization domains include those disclosed in Murre et al. Cell 58:537-544 (1989); the dimerization domain in the retinoic acid receptor, thyroid hormone receptor, other nuclear hormone receptors, see e.g., Kurokawa et al., Genes Dev. 7:1423-1435 (1993); and the dimerization domain in yeast transcription factors GAL4 and HAP1, see e.g., Marmonstein et al., Nature 356:408-414 (1992); Zhang et al., Proc. Natl. Acad. Sci. USA 90:2851-2855 (1993); and U.S. Pat. No. 5,624,818).

In some embodiments, the interaction domain further comprises a linker. The linker links an interaction domain and the first or second fragment of glutamine synthetase. This can be achieved by, e.g., fusing a nucleic acid encoding the first or second glutamine synthetase in frame to a nucleic acid encoding a linker, which is then fused in frame to a nucleic acid encoding an interaction domain. Linkers can be any relatively short, flexible sequence that allows the interaction domain to interact such that the first and second fragment of glutamine synthetase associate to form a functional enzyme and provide a selectable activity.

Non-limiting examples of linkers are known in the art and include those having a sequence of GGPGG (SEQ ID NO: 8), GPGGG (SEQ ID NO: 9), or (GGGGS)n (SEQ ID NOs: 11-14), where n is an integer of 1-4, and G (glycine), P (proline) and S (serine) are single letter amino acid codes. In some embodiments, the linker is a series of glycine and serine residues, for example, that described by Curtis et al. (1991; Proc Natl Acad Sci 88 (13): 5809-5813). In some embodiments, the linker comprises, consisting essentially of, or consisting of a sequence of GGPGG (SEQ ID NO: 8), GPGGG (SEQ ID NO: 9), GGGGSGGGGGS (SEQ ID NO: 10), (GGGGS)n (SEQ ID NOs: 11-14), where n is an integer of 1-4. In some embodiments, the linker comprises, consisting essentially of, or consisting of a sequence of GGPGG (SEQ ID NO: 8), GPGGG (SEQ ID NO: 9), GGGGSGGGGGS (SEQ ID NO: 10) or (GGGGS)n (SEQ ID NOs: 11-12), where n is an integer of 1 or 2.

In some preferred embodiments, the interaction domain is an anti-parallel leucine zipper domain having the following sequence: ALKKELQANKKELAQLK-WELQALKKELAQ EQLEKKLQALEKKLAQLEW-KNQALEKKLAQ (SEQ ID NO: 3), and the linker comprises the sequence of GGGGSGGGGGS (SEQ ID NO: 10). In these embodiments, the configuration of the first and second fragment of glutamine synthetase, linker and interaction domain can be, from the N-terminal to C-terminal, the first fragment of glutamine synthetase-GGGGSGGGGGS-ALKKELQANKKELAQLKWELQALKKELAQ (SEQ ID NO: 7); and EQLEKKLQALEKKLAQLEW-KNQALEKKLAQ-GGGGSGGGGGS (SEQ ID NO: 6)-second fragment of glutamine synthetase. Each of the first and the third polypeptide (e.g., light and heavy chain of an antibody or a fragment thereof) can be linked in both orientations (e.g., N-terminal or C-terminal) to each of the first or the second fragment of glutamine synthetase. For example, in some embodiments, one chain of an antibody is N-terminal to a first fragment of glutamine synthetase and is fused in frame with the first fragment, and the other chain is C-terminal to a second fragment of glutamine synthetase and is fused in frame with the second fragment; in some embodiments, one chain of an antibody is C-terminal to a first fragment of glutamine synthetase and is fused in frame with the first fragment, and the other chain is N-terminal to a second fragment of glutamine synthetase and is fused in frame with the second fragment.

Alternatively, the configuration of the first and second fragment of glutamine synthetase, linker and interaction domain can be, from the N-terminal to C-terminal, EQLEKKLQALEKKLAQLEWKNQALEKKLAQ-GGGGSGGGGGS (SEQ ID NO: 6)-first fragment of glutamine synthetase; and the second fragment of glutamine synthetase-GGGGSGGGGGS-ALKKELQANKKELAQLK-WELQALKKELAQ (SEQ ID NO: 7).

Similarly, each of the first and the third polypeptide (e.g., light and heavy chain of an antibody or a fragment thereof) can be linked in both orientations (e.g., N-terminal or C-terminal) to each of the first or the second fragment of glutamine synthetase.

In some embodiments, the vector disclosed herein or one or both vectors in the expression system disclosed herein may further comprise an internal ribosomal entry site (IRES). IRES facilitates the initiation of translation of an mRNA from an internal site (i.e., a site other than the 5' end of the mRNA). In some embodiments, an IRES occurs at a site between the first nucleic acid and the second nucleic acid; in some embodiments, an IRES occurs at a site between the third nucleic acid and the fourth nucleic acid; in some embodiments, an IRES occurs at sites between both first and second, and third and fourth nucleic acids.

IRES is well known and used in the art. One example of a suitable IRES is the IRES of encephalomyocarditis virus (ECMV), as described in Jang and Wimmer Genes & Development 4 1560 (1990) and Jang, Davies, Kaufman and Wimmer J. Vir. 63 1651 (1989). The residues 335-848 of EMCV form a suitable IRES; other variants or portions of ECMV IRES are known and will be suitable for use in the present invention. A suitable portion or variant of an IRES is one that will confer sufficient translation of the second open reading frame (ORF). Additionally, the 3' end of an IRES may be altered (or mutated) to reduce the efficiency of translation, thereby providing a means to enhance selection and/or amplification methods. For example, the efficiency of the IRES can be decreased by using a sequence previously shown to allow efficient selection and amplification. Aldrich et al., Biotechnol Prog 19, 1433 (2003). In some embodiments, the IRES comprises the sequence of GATGA-TAATACCCTCGAGATCCGTGCCATCATG (SEQ ID NO: 2). Alternative sequences are known, or can be determined by one of ordinary skill in the art.

In some embodiments, the vector disclosed herein or the one or both vectors in the expression system disclosed herein may further comprise an expression augmenting sequence element (EASE). When used in expression vectors, EASE allows the development of stable CHO cell pools for a period of time (e.g., five to seven weeks) that express high levels of recombinant protein. Sec e.g., Aldrich, T. L., Cytotechnology, 28 (1-3): 9-17 (1998). EASE sequences known in the art may be used in the vector or expression system disclosed herein.

The nucleic acids encoding a component of the desired heteromeric complex can be obtained as a cDNA or as a genomic DNA by methods known in the art. For example, messenger RNA coding for a desired component can be isolated from a suitable source employing standard techniques of RNA isolation, and the use of oligo-dT cellulose chromatography to segregate the poly-A mRNA. When the heteromeric complex to be expressed is an antibody, suitable sources of desired nucleic acids can be isolated from mature B cells or a hybridoma culture. In addition, the nucleic acids for use in the invention can be obtained by chemical synthesis.

In some embodiments, one or both vectors of the expression system disclosed herein may further comprise a nucleic acid encoding a different functional selectable marker, in addition to a first and/or second fragment of glutamine synthetase and a polypeptide of a heteromeric complex. As used herein, a "different functional selectable marker" is a protein with a selectable activity different from glutamine synthetase. Well known selectable markers such as zeomy-cin (zeo), neomycin, which confers resistance to the aminoglycoside G-418, Colberre-Garapin et al., J. Mol. Biol. 150:1 (1981), puromycin (PAC), Blasticidin S (BlaS), or GPT which confers resistance to mycophenolic acid, Mulligan & Berg, Proc. Natl. Acad. Sci. USA 78:2072 (1981), etc., and hygro, which confers resistance to hygromycin, Santerre et al., Gene 30: 147 (1984) can be used as different functional selectable markers.

Metabolic enzymes that confer cell survival or induce cell death under prescribed conditions can also be used as a different functional selectable marker. Examples include but are not limited to: dihydrofolate reductase (DHFR); herpes simplex virus thymidine kinase (TK), Wigler et al., Cell 11:223 (1977), hypoxanthine-guanine phosphoribosyltransferase (HGPRT), Szybalska & Szybalski, Proc. Natl. Acad. Sci. USA 48:2026 (1962), and adenine phosphoribosyltransferase (APRT), Lowy et al., Cell 22:817 (1980), which are genes which can be employed in cells lacking TK, HGPRT or APRT, respectively.

Selectable markers that are based on color selection can also be used as a different functional selectable marker. In a particular example, beta-galactosidase can be used, Blau et al., WO 98/44350. Fluorescence markers can also be used in the methods of the present invention, for example, GFP has been used for clonal selection of cells to measure protein interactions in protein-fragment complementation assays, Remy and Michnick, Proc. Natl. Acad. Sci., 96:5394-5399 (1999). Similarly, fluorescein-conjugated methotrexate can be used to detect cells expressing functional glutamine synthetase. An advantage for fluorescent markers is that this selection can be done in any animal cell type and is not restricted to those having a deficiency in a metabolic pathway or does not require a drug sensitivity, e.g., to neomycin.

Thus, in such embodiments, each of the vectors of the expression system disclosed herein comprises a nucleic acid encoding one of two polypeptides that can form a heteromeric complex operably linked to a nucleic acid encoding one of two fragments of glutamine synthetase, as well as a nucleic acid encoding a different, functional selectable marker. Further, the two polypeptides encoded by the nucleic acid of each vector can associate to form a complex, and the two fragments of glutamine synthetase can associate to provide a selectable activity, and the additional selectable marker from one or each vector provides selectable activities different than glutamine synthetase.

For example, in some embodiments, the first vector can further comprise a nucleic acid encoding a first different functional selectable marker (e.g., resistance to neomycin) and the second vector can further comprise a nucleic acid encoding a second different functional selectable marker (e.g., resistance to zeomycin) or only one vector can contain the additional different functional selectable marker. Thus, one vector is transfected into a host cell and selection is applied (e.g., the drug G418 is added to neomycin resistant cells). After selection, conventional methods can be used to determine the presence of the vector and the expression level of the polypeptides encoded by the nucleic acids on the vector, for example by PCR, Southern blot, ELISA, western blot, and the like. Once high-level expression has been obtained, the second vector is transfected into the cell line. While maintaining selection for the first vector, selection is applied for the second selectable marker (e.g., zeomycin resistance) and the presence of the second vector and expression of the respective vector encoded proteins are assessed. In such embodiments, once it has been determined that both vectors are present, selection is applied for expression of functional glutamine synthetase that have associated in the cell to provide a selectable activity as described herein.

Alternatively, in some embodiments, both vectors are transfected simultaneously, and selection is applied at the same time. In some embodiments, only one vector further comprises a different functional selectable marker and both vectors are transfected simultaneously, and selection for the different functional selectable marker is applied. Once it has been determined that both vectors are present, selection is applied for expression of functional glutamine synthetase that have associated in the cell to provide a selectable activity, as described herein.

In yet some other embodiments, vectors can further comprise a nucleic acid encoding different functional selectable markers are each transfected into separate cell lines. Once selection is applied and clones have been identified that express high levels of the proteins encoded by each desired vector, the cells are fused as described in Hori et al. (U.S. Pat. No. 5,916,771). Once fusion is complete, selection is applied for the selectable activity provided by the subunits.

In yet some other embodiments, the first and second vectors that do not comprise a different functional selectable marker are transfected simultaneously with a third vector. The third vector encodes for a separate selectable activity, such as for example, neomycin resistance or beta galactosidase that can allow for a preliminary selection of cells that were successfully transfected. Once this preliminary selection has been performed, selection can be applied for the selectable activity of glutamine synthetase. In these embodiments, equal quantities of the two vectors are transfected while the third vector is transfected at one-third the concentration of the first two vectors (e.g., a ratio of 3:3:1 or 6:6:1 or the like). One of skill in the art will recognize that variations in the ratios are within the scope of the invention.

Vectors and expression systems disclosed herein can be used for producing heteromeric complexes (e.g., antibodies and bispecific antigen binding molecules). For example, vectors or expression systems disclosed herein can be transfected into host cells using methods described above and other methods known in the art. Once it has determined that the vector or the expression system (two vectors) are present in the host cell, the cells then grow under appropriate conditions for the selectable activity of glutamine synthetase such that components of a heteromeric protein are expressed in appropriate amounts to form heteromeric proteins. For host cells that do not express endogenous glutamine synthetase (e.g., glutamine synthetase deficient cells), transfectants can be selected by, e.g., growing the cells in a cell culture medium free of glutamine synthetase. For host cells that express endogenous glutamine synthetase, transfectants may be selected by, e.g., growing the cells in a cell culture medium containing the glutamine synthetase inhibitor methionine sulfoximine (MSX) (e.g., growing the cells in the presence of a toxic level of MSX). The expressed proteins can be harvested and purified from the cells and/or the culture medium.

As used herein, the term "cell culture" is understood to include the growth and propagation of cells outside of a multicellular organism or tissue. Typically, cell culture is performed under sterile, controlled temperature and atmospheric conditions in tissue culture plates (e.g., 10-cm plates, 96 well plates, etc.), or other adherent culture (e.g., on microcarrier beads) or in suspension culture such as in roller bottles. Cultures can be grown in shake flasks, small scale bioreactors, and/or large-scale bioreactors. A bioreactor is a device used to culture cells in which environmental conditions such as temperature, atmosphere, agitation, and/or pH can be monitored and adjusted. A number of companies (e.g., ABS Inc., Wilmington, Del.; Cell Trends, Inc., Middletown, Md.) as well as university and/or government-sponsored organizations (e.g., The Cell Culture Center, Minneapolis, Minn.) offer cell culture services on a contract basis.

Optimal periods for which the cultures are in contact with agents that select for the selectable activity are for longer than the typical period for one normal growth cycle (e.g., for Chinese hamster ovary cells (CHO cells), where one growth cycle has been reported to be approximately 20-22 hours (Rasmussen et al. (1998), Cytotechnology, 28:31-42)). As such, in some embodiments, the cultures comprise selectable conditions, e.g., drugs, metabolites, or color substrates, preferably for at least about one day, more preferably for at least about 3 days, and even more preferably for at least about 5 days or at least about 7 days.

In some embodiments, vectors or expression systems disclosed herein can be transfected into a suitable host cell. In some embodiments, the host cell is a mammalian cell. A wide variety of mammalian cells suitable for growth in culture are available from, for example, the American Type Culture Collection (ATCC, Manassas, Va.) and NRRL (Peoria, 111.). Non-limiting examples of mammalian cells typically used in the industrial or academic laboratory include CHO, VERO, BHK, HeLa, Cos, CV1, MDCK, 293, 3T3, PC12, myeloma (e.g., NSO), and WI38 cell lines. In addition, new mammalian cell lines can be established using methods well known by those skilled in the art (e.g., by transformation, viral infection, and/or selection). In some embodiments, the host cell is CHO, VERO, BHK, HeLa, Cos, CV1, MDCK, 293, 3T3, PC12, or NSO cells. In some embodiments, the host cell is CHO cells. CHO cells are easy to manipulate as adherent or suspension cultures and exhibit relatively good genetic stability.

In some embodiments, the host cell is a cell that does not express endogenous glutamine synthetase (e.g., a mammalian cell with endogenous glutamine synthetase knocked out). Cell lines that do not express endogenous glutamine synthetase include the glutamine synthetase deficient CHO cells such as CHOZN® GS−/− ZFN-modified CHO cells (Sigma Aldrich Fine Chemicals, St. Louis MO). Glutamine synthetase deficient CHO cells (or other mammalian cells) can also be prepared using methods that are known in the art.

In some embodiments, the host cell is a non-mammalian cell. Non-mammalian cell lines that can be used, for example, plant cell lines, insect cell lines (e.g., sf9), yeast cells or bacterial cells such as E. coli.

Heteromeric complexes (e.g., monoclonal antibodies) expressed using the vectors and expression systems disclosed herein can be recovered from the cell culture, e.g., from the host cell in cases where the heteromeric complexes are not secreted, and from the culture media in cases where the heteromeric complexes are secreted by the cells. However, the expression systems also encompass engineered host cells that express the heteromeric complexes anchored in the cell membrane.

Heteromeric complexes (e.g., monoclonal antibodies) expressed by the methods of the invention can be harvested. In addition, the complexes can be purified, or partially purified, from such culture or component (e.g., from culture medium or cell extracts) using known processes. The phrase "partially purified" means that some fractionation procedure, or procedures, have been carried out, but that more polypeptide species (at least 10%) than the desired protein is present. By "purified" is meant that the protein is essentially homogeneous, e.g., less than 1%, less than 0.5%, less than 0.3%, or less than 0.1% contaminating proteins are present. Purification procedures can include but are not limited to one or more steps of filtration, centrifugation, precipitation, phase separation, affinity purification, gel filtration, ion exchange chromatography, size exclusion chromatography (SEC), hydrophobic interaction chromatography (HIC); using such resins as phenyl ether, butyl ether, or propyl ether), HPLC, or some combination of above.

The invention also optionally encompasses further formulating the proteins. By the term "formulating" is meant that the proteins can be buffer exchanged, sterilized, bulk-packaged and/or packaged for a final user. For purposes of the invention, the term "sterile bulk form" means that a formulation is free, or essentially free, of microbial contamination (to such an extent as is acceptable for food and/or drug purposes), and is of defined composition and concentration.

The term "sterile unit dose form" means a form that is appropriate for the customer and/or patient administration or consumption. Such compositions can comprise an effective amount of the protein, in combination with other components such as a physiologically acceptable diluent, carrier, or excipient. The term "physiologically acceptable" means a non-toxic material that does not interfere with the effectiveness of the biological activity of the active ingredient(s).

The invention will be more fully understood by reference to the following examples. The examples should not, however, be construed as limiting the scope of the invention.

EXAMPLES

Example 1. Identification of Suitable Amino Acid Positions of Glutamine Synthetase as Sites for Splitting the Polypeptide Highly solvent exposed residues on multiple green (and yellow) fluorescence proteins have been targeted for splitting the fluorescence proteins, and polypeptide fragments generated by splitting at those amino acid positions were found to be able to interact/associate to form a functional protein. Similarly, highly solvent exposed residues were also used to split the protein Luciferase. See Ishikawa et. al., Protein Eng Des Sel. Dec; 25 (12): 813-20 (2012). However, contrary to what was reported in literature, we found that solvent accessibility of the backbone atoms (e.g., N, CA, C, O) only, as opposed to the complete residue, can be used to rank exposure of residues and such ranking was used to identify splitting sites.

Structures of selected glutamine synthetase (GS) from different species, including GS from maize, human, canine, and were obtained from the Protein Data Bank to help building a model of the mouse GS. The methionine sulfoximine (MSX) bound structure of human GS was used to build a homology model of the decamer of the mouse GS. Using the model, we analyzed solvent accessibility of the backbone atoms of the mouse glutamine synthetase and identified nine potential amino acid positions at which to split the polypeptide such that two glutamine synthetase fragments obtained by splitting the polypeptide at each position can interact/associate to form a functional glutamine synthetase. The nine amino acid positions were K52, E55, D92, G187, G245, R262, K291, G302 and D311 of the mouse glutamine synthetase (SEQ ID NO:1), with two possible ways to split the polypeptide at each position as listed in Table 1 below.

TABLE 1

| List of amino acid positions for splitting glutamine synthetase | | |
|---|---|---|
| AA position | N-terminal half | C-terminal half |
| 52 | 1-51 K52 | 52-373 |
| | 1-52 | 53-373 |
| 55 | 1-54 E55 | 55-373 |
| | 1-55 | 56-373 |
| 92 | 1-91 D92 | 92-373 |
| | 1-92 | 93-373 |
| 245 | 1-244 G245 | 245-373 |
| | 1-245 | 246-373 |
| 187 | 1-186 G187 | 187-373 |
| | 1-187 | 188-373 |
| 262 | 1-261 R262 | 262-373 |
| | 1-263 | 264-373 |
| 311 | 1-310 D311 | 311-373 |
| | 1-311 | 312-373 |

TABLE 1-continued

| List of amino acid positions for splitting glutamine synthetase | | |
|---|---|---|
| AA position | N-terminal half | C-terminal half |
| 302 | 1-301 G302 | 302-373 |
| | 1-302 | 303-373 |
| 291 | 1-291 K291 | 292-373 |
| | 1-292 | 293-373 |

Example 2. Expression of Glutamine Synthetase Using Two Vectors

Among the nine splitting sites identified in Example 1, five (K52, E55, G187, D92 and G245) were tested in this experiment. For each splitting site, a pair of linear plasmids as well as a pair of circular plasmids were constructed. An anti-parallel leucine zipper was used as the interaction domain together with a linker having the sequence of GGGGSGGGGS (SEQ ID NO: 12). Table 2 below shows the list of vectors constructed in this experiment. In Table 2, 51-L1 stands for a pair of linear plasmids carrying amino acid residues 1-51 and 52-373 respectively, of glutamine synthetase (SEQ ID NO:1); 51-L2 refers to the duplicate of 51-L1. 51-C1 refers to a pair of circular plasmids carrying residues 1-51 and 52-373 respectively, of glutamine synthetase (SEQ ID NO:1); 51-C2 refers to the duplicate of 51-C1. Similar to 51-L1, L2, C1, and C2, constructs 52-L1, L2, C1, C2 were also made since split sites separated by one amino acid may have an impact on interaction/association of two glutamine synthetase fragments. See Ishikawa et. al. Protein Eng Des Sel., 25 (12): 813-20 (2012).

Figure 2:
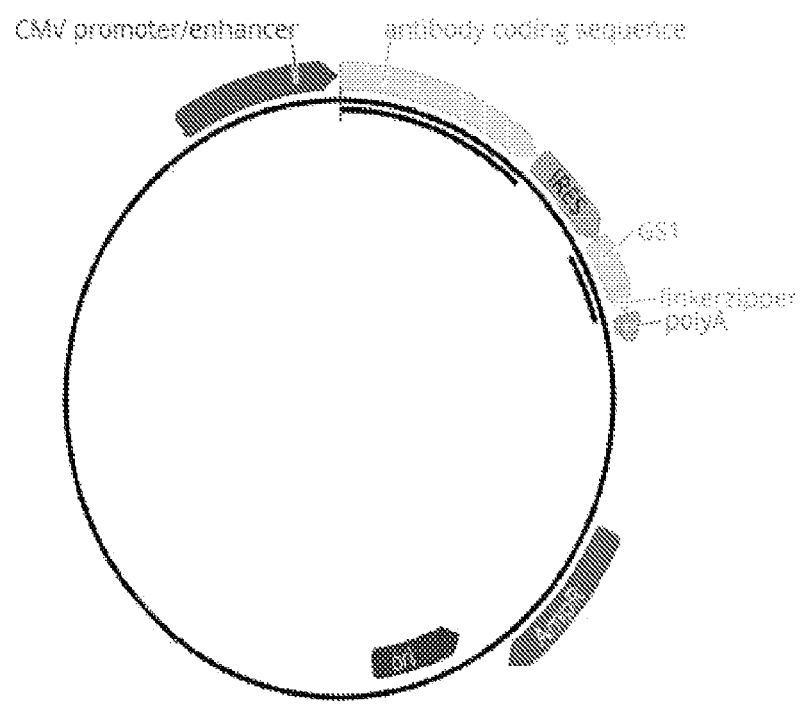
FIG. 2 shows an exemplary plasmid map of the vectors used in the Examples. The top panel provides a vector map of a vector comprising a CMV promoter/enhancer, a first nucleic acid comprising an antibody coding sequence, and IRES, a second nucleic acid comprising a first fragment of glutamine synthetase (GS1), a linker, an interaction domain (linker/zipper), and a polyadenylation signal (PolyA). The bottom panel provides a vector map of a vector comprising a CMV promoter/enhancer, a third nucleic acid comprising an antibody coding sequence, an IRES, an interaction domain (linker/zipper), a fourth nucleic acid comprising a second fragment of glutamine synthetase (GS1), and a polyadenylation signal (PolyA).
Figure 2:
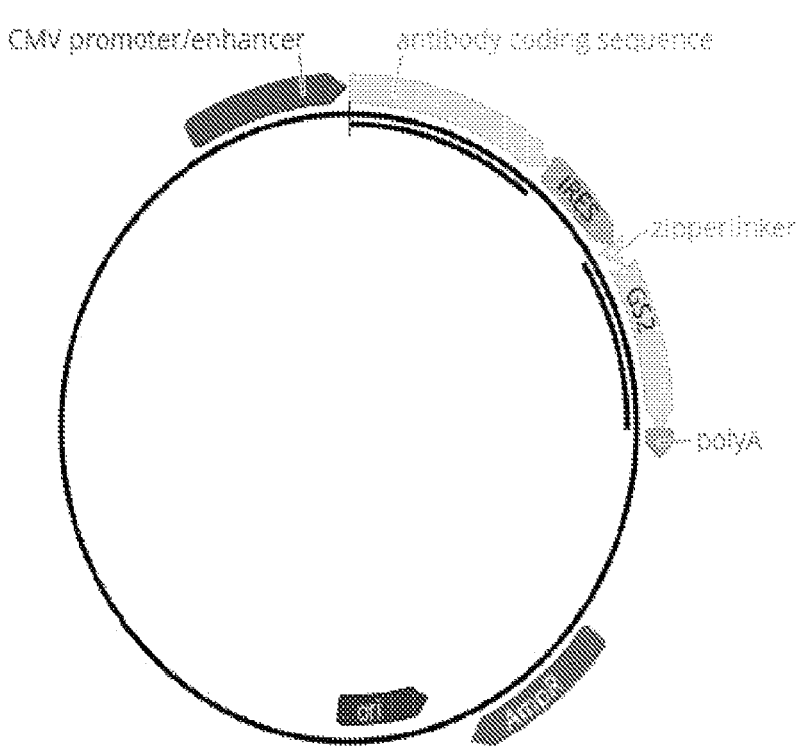

FIG. 2 shows the map of the two vectors of the expression system used in the experiments. Table 3 below shows the configuration of the two glutamine synthetase fragments together with the interaction domain (the underlined sequences) and linker sequence in each plasmid prepared.

TABLE 2

| List of vectors constructed | | | |
|---|---|---|---|
| | CLD Abbreviation | N-terminal GS* fragment | C-terminal GS fragment |
| 1 | 51-L1, L2, C1, C2 | 1-51 K52 | 52-373 |
| | 52-L1, L2, C1, C2 | 1-52 | 53-373 |
| 2 | 54-L1, L2, C1, C2 | 1-54 E55 | 55-373 |
| | 55-L1, L2, C1, C2 | 1-55 | 56-373 |
| 3 | 186-L1, L2, C1, C2 | 1-186 G187 | 187-373 |
| | 187-L1, L2, C1, C2 | 1-187 | 188-373 |
| 4 | 91-L1, L2, C1, C2 | 1-91 D92 | 92-373 |
| | 92-L1, L2, C1, C2 | 1-92 | 93-373 |
| 5 | 244-L1, L2, C1, C2 | 1-244 G245 | 245-373 |
| | 245-L1, L2, C1, C2 | 1-245 | 246-373 |

*GS: glutamine synthetase

TABLE 3

Configuration of Glutamine synthetase fragment, interaction domain and linker

| N-terminal GS fragment | C-terminal fragment |
|---|---|
| 1 >1-51 K52 | >52-373 |
| MATSASSHLNKGIKQMYMSLPQGEKVQAM | EQLEKKLQALEKKLAQLEWKNQALEK |
| YIWVDGTGEGLRCKTRTLDCEPGGGGSGG | KLAQGGGGSGGGGSKCVEELPEWNFD |
| GGSALKKELQANKKELAQLKWELQALKKE | GSSTFQSEGSNSDMYLHPVAMFRDPFR |
| LAQ | KDPNKLVLCEVFKYNRKPAETNLRHIC |
| (SEQ ID NO: 15) | KRIMDMVSNQHPWFGMEQEYTLMGTD |
| | GHPFGWPSNGFPGPQGPYYCGVGADKA |

TABLE 3-continued

| Configuration of Glutamine synthetase fragment, interaction domain and linker | | |
| --- | --- | --- |
| | N-terminal GS fragment | C-terminal fragment |
| | | YGRDIVEAHYRACLYAGVKITGTNAEV MPAQWEFQIGPCEGIRMGDHLWIARFIL HRVCEDFGVIATFDPKPIPGNWNGAGC HTNFSTKAMREENGLKCIEEAIDKLSKR HQYHIRAYDPKGGLDNARRLTGFHETS NINDFSAGVANRGASIRIPRTVGQEKKG YFEDRRPSANCDPYAVTEAIVRTCLLNE TGDEPFQYKN (SEQ ID NO: 16) |
| | >1-52 MATSASSHLNKGIKQMYMSLPQGEKVQAM YIWVDGTGEGLRCKTRTLDCEPKGGGGSG GGGSALKKELQANKKELAQLKWELQALK KELAQ (SEQ ID NO: 17) | >53-373 EQLEKKLQALEKKLAQLEWKNQALEK KLAQGGGGSGGGGSCVEELPEWNEDGS STFQSEGSNSDMYLHPVAMFRDPFRKD PNKLVLCEVFKYNRKPAETNLRHICKRI MDMVSNQHPWFGMEQEYTLMGTDGH PFGWPSNGFPGPQGPYYCGVGADKAYG RDIVEAHYRACLYAGVKITGTNAEVMP AQWEFQIGPCEGIRMGDHLWIARFILHR VCEDFGVIATFDPKPIPGNWNGAGCHT NESTKAMREENGLKCIEEAIDKLSKRHQ YHIRAYDPKGGLDNARRLTGFHETSNIN DFSAGVANRGASIRIPRTVGQEKKGYFE DRRPSANCDPYAVTEAIVRTCLLNETGD EPFQYKN (SEQ ID NO: 18) |
| 2 | >1-54 E55 MATSASSHLNKGIKQMYMSLPQGEKVQAM YIWVDGTGEGLRCKTRTLDCEPKCV GGGGSGGGGSALKKELQANKKELAQLKW ELQALKKELAQ (SEQ ID NO: 19) | >55-373 EQLEKKLQALEKKLAQLEWKNQALEK KLAQGGGGSGGGGSEELPEWNFDGSST FQSEGSNSDMYLHPVAMFRDPFRKDPN KLVLCEVFKYNRKPAETNLRHICKRIMD MVSNQHPWFGMEQEYTLMGTDGHPFG WPSNGFPGPQGPYYCGVGADKAYGRDI VEAHYRACLYAGVKITGTNAEVMPAQ WEFQIGPCEGIRMGDHLWIARFILHRVC EDFGVIATFDPKPIPGNWNGAGCHTNFS TKAMREENGLKCIEEAIDKLSKRHQYHI RAYDPKGGLDNARRLTGFHETSNINDES AGVANRGASIRIPRTVGQEKKGYFEDRR PSANCDPYAVTEAIVRTCLLNETGDEPF QYKN (SEQ ID NO: 20) |
| | >1-55 MATSASSHLNKGIKQMYMSLPQGEKVQAM YIWVDGTGEGLRCKTRTLDCEPKCVEGGG GSGGGGSALKKELQANKKELAQLKWELQA LKKELAQ (SEQ ID NO: 21) | >56-373 EQLEKKLQALEKKLAQLEWKNQALEK KLAQGGGGSGGGGSELPEWNFDGSSTF QSEGSNSDMYLHPVAMFRDPFRKDPNK LVLCEVFKYNRKPAETNLRHICKRIMD MVSNQHPWFGMEQEYTLMGTDGHPFG WPSNGFPGPQGPYYCGVGADKAYGRDI VEAHYRACLYAGVKITGTNAEVMPAQ WEFQIGPCEGIRMGDHLWIARFILHRVC EDFGVIATFDPKPIPGNWNGAGCHTNFS TKAMREENGLKCIEEAIDKLSKRHQYHI RAYDPKGGLDNARRLTGFHETSNINDFS AGVANRGASIRIPRTVGQEKKGYFEDRR PSANCDPYAVTEAIVRTCLLNETGDEPF QYKN (SEQ ID NO: 22) |
| 3 | >1-91 D92 MATSASSHLNKGIKQMYMSLPQGEKVQAM YIWVDGTGEGLRCKTRTLDCEPKCVEELPE WNFDGSSTFQSEGSNSDMYLHPVAMFRDP FRKGGGGSGGGGSALKKELQANKKELAQL KWELQALKKELAQ (SEQ ID NO: 23) | >92-373 EQLEKKLQALEKKLAQLEWKNQALEK KLAQGGGGSGGGGSDPNKLVLCEVFKY NRKPAETNLRHICKRIMDMVSNQHPWF GMEQEYTLMGTDGHPFGWPSNGFPGPQ GPYYCGVGADKAYGRDIVEAHYRACL YAGVKITGTNAEVMPAQWEFQIGPCEGI RMGDHLWIARFILHRVCEDFGVIATFDP KPIPGNWNGAGCHTNFSTKAMREENGL KCIEEAIDKLSKRHQYHIRAYDPKGGLD NARRLTGFHETSNINDFSAGVANRGASI RIPRTVGQEKKGYFEDRRPSANCDPYA VTEAIVRTCLLNETGDEPFQYKN (SEQ ID NO: 24) |

TABLE 3-continued

Configuration of Glutamine synthetase fragment, interaction
domain and linker

| N-terminal GS fragment | C-terminal fragment |
|---|---|
| >1-92<br>MATSASSHLNKGIKQMYMSLPQGEKVQAM<br>YIWVDGTGEGLRCKTRTLDCEPKCVEELPE<br>WNFDGSSTFQSEGSNSDMYLHPVAMFRDP<br>FRKDGGGGSGGGGSALKKELQANKKELAQ<br>LKWELQALKKELAQ<br>(SEQ ID NO: 25) | >93-373<br>EQLEKKLQALEKKLAQLEWKNQALEK<br>KLAQGGGGSGGGGSPNKLVLCEVFKYN<br>RKPAETNLRHICKRIMDMVSNQHPWFG<br>MEQEYTLMGTDGHPFGWPSNGFPGPQG<br>PYYCGVGADKAYGRDIVEAHYRACLY<br>AGVKITGTNAEVMPAQWEFQIGPCEGIR<br>MGDHLWIARFILHRVCEDFGVIATFDPK<br>PIPGNWNGAGCHTNESTKAMREENGLK<br>CIEEAIDKLSKRHQYHIRAYDPKGGLDN<br>ARRLTGFHETSNINDFSAGVANRGASIRI<br>PRTVGQEKKGYFEDRRPSANCDPYAVT<br>EAIVRTCLLNETGDEPFQYKN<br>(SEQ ID NO: 26) |
| 4  >1-186 G187<br>MATSASSHLNKGIKQMYMSLPQGEKVQAM<br>YIWVDGTGEGLRCKTRTLDCEPKCVEELPE<br>WNFDGSSTFQSEGSNSDMYLHPVAMFRDP<br>FRKDPNKLVLCEVFKYNRKPAETNLRHICK<br>RIMDMVSNQHPWFGMEQEYTLMGTDGHP<br>FGWPSNGFPGPQGPYYCGVGADKAYGRDI<br>VEAHYRACLYAGGGGSGGGGSALKKELQA<br>NKKELAQLKWELQALKKELAQ<br>(SEQ ID NO: 27) | >187-373<br>EQLEKKLQALEKKLAQLEWKNQALEK<br>KLAQGGGGSGGGGSGVKITGTNAEVMP<br>AQWEFQIGPCEGIRMGDHLWIARFILHR<br>VCEDFGVIATFDPKPIPGNWNGAGCHT<br>NFSTKAMREENGLKCIEEAIDKLSKRHQ<br>YHIRAYDPKGGLDNARRLTGFHETSNIN<br>DFSAGVANRGASIRIPRTVGQEKKGYFE<br>DRRPSANCDPYAVTEAIVRTCLLNETGD<br>EPFQYKN<br>(SEQ ID NO: 28) |
| >1-187<br>MATSASSHLNKGIKQMYMSLPQGEKVQAM<br>YIWVDGTGEGLRCKTRTLDCEPKCVEELPE<br>WNFDGSSTFQSEGSNSDMYLHPVAMFRDP<br>FRKDPNKLVLCEVFKYNRKPAETNLRHICK<br>RIMDMVSNQHPWFGMEQEYTLMGTDGHP<br>FGWPSNGFPGPQGPYYCGVGADKAYGRDI<br>VEAHYRACLYAGGGGSGGGGSALKKELQ<br>ANKKELAQLKWELQALKKELAQ<br>(SEQ ID NO: 29) | >188-373<br>EQLEKKLQALEKKLAQLEWKNQALEK<br>KLAQGGGGSGGGGSVKITGTNAEVMPA<br>QWEFQIGPCEGIRMGDHLWIARFILHRV<br>CEDFGVIATFDPKPIPGNWNGAGCHTNF<br>STKAMREENGLKCIEEAIDKLSKRHQYH<br>IRAYDPKGGLDNARRLTGFHETSNINDF<br>SAGVANRGASIRIPRTVGQEKKGYFEDR<br>RPSANCDPYAVTEAIVRTCLLNETGDEP<br>FQYKN<br>(SEQ ID NO: 30) |
| 5  >1-244 G245<br>MATSASSHLNKGIKQMYMSLPQGEKVQAM<br>YIWVDGTGEGLRCKTRTLDCEPKCVEELPE<br>WNFDGSSTFQSEGSNSDMYLHPVAMFRDP<br>FRKDPNKLVLCEVFKYNRKPAETNLRHICK<br>RIMDMVSNQHPWFGMEQEYTLMGTDGHP<br>FGWPSNGFPGPQGPYYCGVGADKAYGRDI<br>VEAHYRACLYAGVKITGTNAEVMPAQWEF<br>QIGPCEGIRMGDHLWIARFILHRVCEDFGVI<br>ATFDPKPIPGGGGSGGGGSALKKELQANKK<br>ELAQLKWELQALKKELAQ<br>(SEQ ID NO: 31) | >245-373<br>EQLEKKLQALEKKLAQLEWKNQALEK<br>KLAQGGGGSGGGGSGNWNGAGCHTNF<br>STKAMREENGLKCIEEAIDKLSKRHQYH<br>IRAYDPKGGLDNARRLTGFHETSNINDF<br>SAGVANRGASIRIPRTVGQEKKGYFEDR<br>RPSANCDPYAVTEAIVRTCLLNETGDEP<br>FQYKN<br>(SEQ ID NO: 32) |
| >1-245<br>MATSASSHLNKGIKQMYMSLPQGEKVQAM<br>YIWVDGTGEGLRCKTRTLDCEPKCVEELPE<br>WNFDGSSTFQSEGSNSDMYLHPVAMFRDP<br>FRKDPNKLVLCEVFKYNRKPAETNLRHICK<br>RIMDMVSNQHPWFGMEQEYTLMGTDGHP<br>FGWPSNGFPGPQGPYYCGVGADKAYGRDI<br>VEAHYRACLYAGVKITGTNAEVMPAQWEF<br>QIGPCEGIRMGDHLWIARFILHRVCEDFGVI<br>ATFDPKPIPGGGGSGGGGSALKKELQANK<br>KELAQLKWELQALKKELAQ<br>(SEQ ID NO: 33) | >246-373<br>EQLEKKLQALEKKLAQLEWKNQALEK<br>KLAQGGGGSGGGGSNWNGAGCHTNFS<br>TKAMREENGLKCIEEAIDKLSKRHQYHI<br>RAYDPKGGLDNARRLTGFHETSNINDFS<br>AGVANRGASIRIPRTVGQEKKGYFEDRR<br>PSANCDPYAVTEAIVRTCLLNETGDEPF<br>QYKN<br>(SEQ ID NO: 34) |

Each pair of the plasmid constructs were transfected into glutamine synthetase knock out host CHO cells (endogenous glutamine synthetase gene knocked out using recombinant DNA technology), which is a glutamine synthetase deficient, serum free suspension growth adapted CHO cell line derived from CHO-K1 (Kao and Puck, 1968). These host cells are auxotrophic for glutamine, and therefore require presence of glutamine in the growth medium for survival. The host cells were co-transfected with each of the two plasmid constructs using a standard electroporation procedure. Transfected cells that had successfully integrated a fully-functional GS enzyme were able to grow in media lacking glutamine. After transfection, the cells were grown in selective growth media, lacking glutamine, until viability reached >90%. The resulting cell population was referred to as the stable pool. The recovery data is presented in FIGS. 3 and 4. In both figures, CS9 represents a CHO DHFR-cell line derived from DuxB11, pGS is a vector carrying the DNA of full Glutamine Synthetase, which was used as a positive control.

Figure 3:
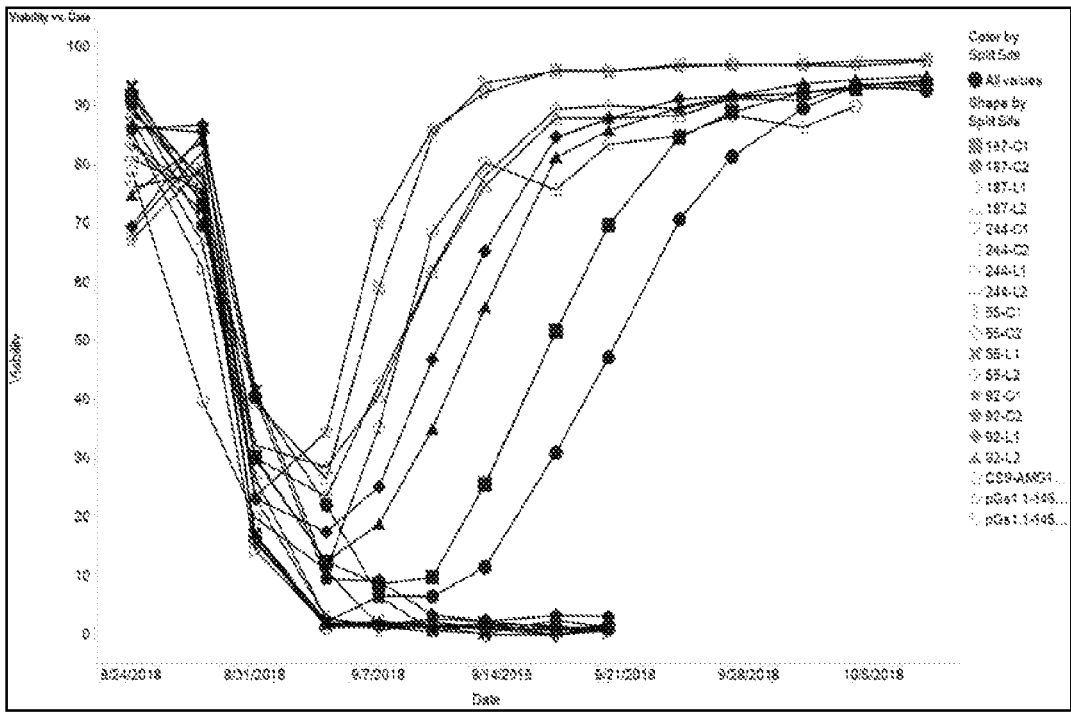
FIG. 3 shows cell recovery data of various control cell lines (CS9, pGS) and cells transfected with plasmids comprising glutamine synthetase fragments generated by splitting the polypeptide at sites 1-55, 1-92, 1-187, and 1-244 of SEQ ID NO:1 in both linear (L1, L2) and circular format (C1, C2). Cells carrying split site 1-187 recovered in both the linear and circular format while the site 1-92 recovered in the linear format.
Figure 4:
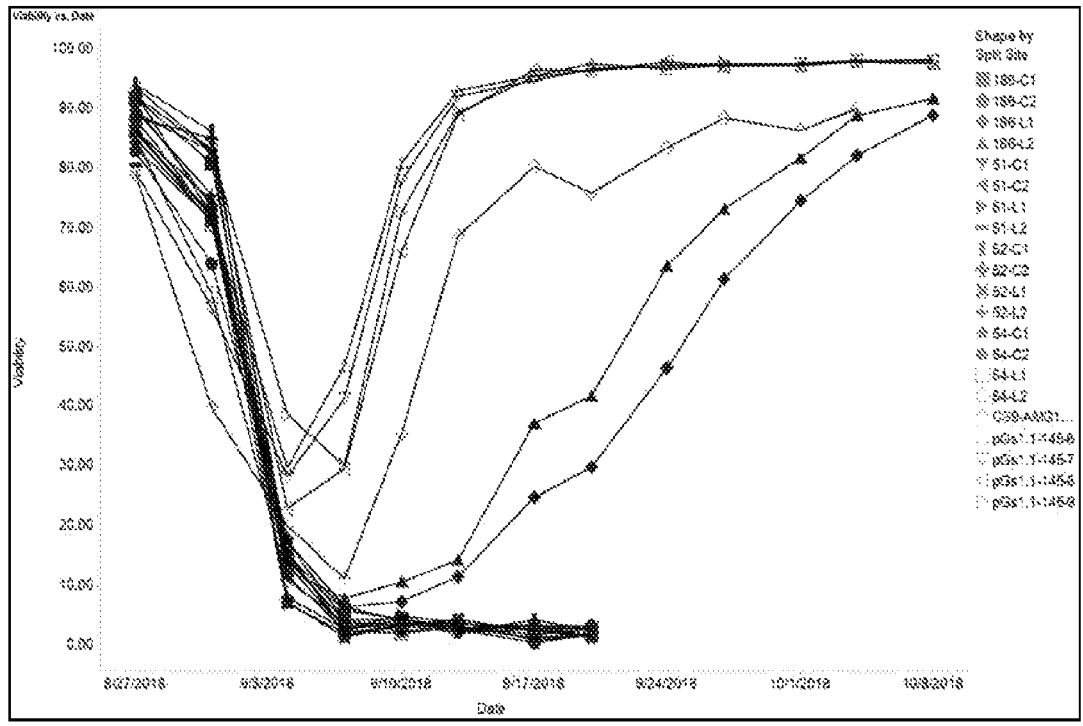
FIG. 4 shows cells recovery data of cells carrying split site 1-186 in the linear format.

Glutamine synthetase knock out CHO cells transfected with both linear and circular plasmids comprising glutamine synthetase fragments generated by splitting at amino acid position G187 were able to grow in cell culture medium lacking glutamine (FIGS. 3 and 4). In addition, glutamine synthetase knock out CHO cells transfected with linear plasmids comprising glutamine synthetase fragments generated by splitting at amino acid position D92 were able to grow in cell culture medium lacking glutamine (FIG. 3).

All references cited in this application are incorporated by reference herein.

---

What is claimed:

1. An expression system comprising:
a) a first vector comprising a first nucleic acid encoding a first polypeptide, wherein the transcription of the first nucleic acid is operably linked to the transcription of a second nucleic acid encoding a first fragment of glutamine synthetase fused to a first interaction domain, and
b) a second vector comprising a third nucleic acid encoding a third polypeptide, wherein the transcription of the third nucleic acid is operably linked to the transcription of a fourth nucleic acid encoding a second fragment of glutamine synthetase fused to a second interaction domain,
wherein the first polypeptide is capable of associating with the third polypeptide to form a heteromeric complex,
wherein the first and second fragments of glutamine synthetase are generated by splitting the glutamine synthetase polypeptide between amino acid positions equivalent to D92/P93, A186/G187, or G187/V188 of SEQ ID NO: 1 according to sequence alignment, the first fragment and second fragment associate via the first and second interaction domains to provide a selectable activity, and
wherein the expression system is capable of being transfected into mammalian cells and improving selection of the cells.

2. The expression system of claim 1, wherein
a) the first fragment of glutamine synthetase is an N-terminal fragment of glutamine synthetase and the second fragment of glutamine synthetase is a C-terminal fragment of glutamine synthetase, or
b) the first fragment of glutamine synthetase is a C-terminal fragment of glutamine synthetase and the second fragment of glutamine synthetase is an N-terminal fragment of glutamine synthetase.

3. The expression system of claim 1, wherein the glutamine synthetase comprises the amino acid sequence of SEQ ID NO: 1, and the first and second fragments of glutamine synthetase are generated by splitting the glutamine synthetase polypeptide between amino acid positions equivalent to D92/P93, A186/G187, or G187/V188 of SEQ ID NO: 1.

4. The expression system of claim 1, wherein the first and second fragments of glutamine synthetase are generated by splitting the glutamine synthetase polypeptide between amino acid positions equivalent to A186/G187 or G187/V188 of SEQ ID NO: 1.

5. The expression system of claim 1, wherein the glutamine synthetase is a mammalian glutamine synthetase having an amino acid sequence different from SEQ ID NO:1, and the first and second fragments of glutamine synthetase are generated by splitting the glutamine synthetase polypeptide between at an amino acid positions equivalent to D92/P93, A186/G187, or G187/V188, of SEQ ID NO:1 according to sequence alignment.

6. The expression system of claim 3, wherein
a) the first glutamine synthetase fragment comprises amino acid residues 1 to 92 of SEQ ID NO: 1 and the second glutamine synthetase fragment comprises amino acid residues 93 to 373 of SEQ ID NO: 1;

b) the first glutamine synthetase fragment comprises amino acid residues 1 to 186 of SEQ ID NO: 1 and the second glutamine synthetase fragment comprises amino acid residues 187 to 373 of SEQ ID NO: 1; or c) the first glutamine synthetase fragment comprises amino acid residues 1 to 187 of SEQ ID NO: 1 and the second glutamine synthetase fragment comprises amino acid residues 188 to 373 of SEQ ID NO: 1.

7. The expression system of claim 1, wherein one or both the first and second vectors further comprise an internal ribosomal entry site (IRES) and/or an expression augmenting sequence element (EASE).

8. The expression system of claim 1, wherein each of the first and second interaction domains is a leucine zipper or an anti-parallel leucine zipper polypeptide.

9. The expression system of claim 1, wherein each of the first and second interaction domains further comprises a linker having a sequence selected from GGPGG (SEQ ID NO: 8), GPGGG (SEQ ID NO: 9), GGGGSGGGGGS (SEQ ID NO: 10), GGGGS (SEQ ID NO: 11) and GGGGSGGGGS (SEQ ID NO: 12).

10. The expression system of claim 9, wherein a) The first interaction domain is fused to the N-terminus of the first glutamine synthetase fragment and has the amino acid sequence of GGGGSGGGGSALKKELQANKKELAQLK-WELQALKKELAQ (SEQ ID NO: 7) and the second interaction domain is fused to the C-terminus of the second glutamine synthetase fragment and has the amino acid sequence of EQLEKKLQALEKKLAQLEW-KNQALEKKLAQGGGGSGGGGS (SEQ ID NO: 6); or b) The first interaction domain is fused to the C-terminus of the first glutamine synthetase fragment and has the amino acid sequence of EQLEKKLQALEKKLAQLEW-KNQALEKKLAQGGGGSGGGGS (SEQ ID NO: 6) and the second interaction domain is fused to the N-terminus of the second glutamine synthetase fragment and has the amino acid sequence of GGGGSGGGGSALKKELQANKKELAQLK-WELQALKKELAQ (SEQ ID NO: 7).

11. The expression system of claim 1, wherein the heteromeric complex is an antibody, an antigen binding fragment of an antibody or a bispecific antigen binding molecule.

12. The expression system of claim 1, wherein a) the first polypeptide is a heavy chain of an antibody or a fragment thereof and the third polypeptide is a light chain of an antibody or a fragment thereof; or b) the first polypeptide is a light chain of an antibody or a fragment thereof and the third polypeptide is a heavy chain of an antibody or a fragment thereof.

13. The expression system of claim 1, wherein one or both the first and second vector further comprises an additional nucleic acid encoding a selectable marker, wherein the selectable marker confers resistance to an agent selected from zeomycin, neomycin, puromycin, Blasticidin S, and mycophenolic acid.

14. A host cell comprising the expression system of claim 1.

15. The host cell of claim 14, wherein the host cell is a Chinese hamster ovary (CHO), VERO, baby hamster kidney (BHK), HeLa, CV-1 in Origin with SV40 genes (Cos), Madin-Darby canine kidney (MDCK), HEK293, 3T3, murine non-secreting (NSO), or Wistar Institute-38 (WI38) cell.

16. The host cell of claim 14 wherein the host cell lacks endogenous glutamine synthetase.

17. A method of producing an antibody heavy chain or a fragment thereof and an antibody light chain or a fragment thereof, the method comprising culturing a host cell comprising the expression system of claim 12 under conditions wherein the heteromeric complex is expressed by the host cell.

18. The method of claim 17, further comprising isolating the heteromeric complex.

* * * * *

SEQUENCE LISTING

```
<160> NUMBER OF SEQ ID NOS: 39

<210> SEQ ID NO 1
<211> LENGTH: 373
<212> TYPE: PRT
<213> ORGANISM: Artificial Sequence
<220> FEATURE:
<223> OTHER INFORMATION: mouse glutamine synthetase amino acid sequence

<400> SEQUENCE: 1

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
            35                  40                  45

Cys Glu Pro Lys Cys Val Glu Glu Leu Pro Glu Trp Asn Phe Asp Gly
    50                  55                  60

Ser Ser Thr Phe Gln Ser Glu Gly Ser Asn Ser Asp Met Tyr Leu His
65                  70                  75                  80

Pro Val Ala Met Phe Arg Asp Pro Phe Arg Lys Asp Pro Asn Lys Leu
                85                  90                  95

Val Leu Cys Glu Val Phe Lys Tyr Asn Arg Lys Pro Ala Glu Thr Asn
            100                 105                 110

Leu Arg His Ile Cys Lys Arg Ile Met Asp Met Val Ser Asn Gln His
            115                 120                 125

Pro Trp Phe Gly Met Glu Gln Glu Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
            165                 170                 175

Glu Ala His Tyr Arg Ala Cys Leu Tyr Ala Gly Val Lys Ile Thr Gly
            180                 185                 190

Thr Asn Ala Glu Val Met Pro Ala Gln Trp Glu Phe Gln Ile Gly Pro
            195                 200                 205

Cys Glu Gly Ile Arg Met Gly Asp His Leu Trp Ile Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Cys Ile Glu Glu
            260                 265                 270

Ala Ile Asp Lys Leu Ser Lys Arg His Gln Tyr His Ile Arg Ala Tyr
            275                 280                 285

Asp Pro Lys Gly Gly Leu Asp Asn Ala Arg Arg Leu Thr Gly Phe His
```

```
            290                 295                 300

Glu Thr Ser Asn Ile Asn Asp Phe Ser Ala Gly Val Ala Asn Arg Gly
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Tyr Ala Val Thr
                340                 345                 350

Glu Ala Ile Val Arg Thr Cys Leu Leu Asn Glu Thr Gly Asp Glu Pro
        355                 360                 365

Phe Gln Tyr Lys Asn
    370

<210> SEQ ID NO 2
<211> LENGTH: 33
<212> TYPE: DNA
<213> ORGANISM: Artificial Sequence
<220> FEATURE:
<223> OTHER INFORMATION: artificial nucleotide

<400> SEQUENCE: 2
gatgataata ccctcgagat ccgtgccatc atg                                33

<210> SEQ ID NO 3
<211> LENGTH: 59
<212> TYPE: PRT
<213> ORGANISM: Artificial Sequence
<220> FEATURE:
<223> OTHER INFORMATION: artificial peptide

<400> SEQUENCE: 3

Ala Leu Lys Lys Glu Leu Gln Ala Asn Lys Lys Glu Leu Ala Gln Leu
1               5                   10                  15

Lys Trp Glu Leu Gln Ala Leu Lys Lys Glu Leu Ala Gln Glu Gln Leu
            20                  25                  30

Glu Lys Lys Leu Gln Ala Leu Glu Lys Lys Leu Ala Gln Leu Glu Trp
        35                  40                  45

Lys Asn Gln Ala Leu Glu Lys Lys Leu Ala Gln
    50                  55

<210> SEQ ID NO 4
<211> LENGTH: 29
<212> TYPE: PRT
<213> ORGANISM: Artificial Sequence
<220> FEATURE:
<223> OTHER INFORMATION: artificial peptide

<400> SEQUENCE: 4

Ala Leu Lys Lys Glu Leu Gln Ala Asn Lys Lys Glu Leu Ala Gln Leu
1               5                   10                  15

Lys Trp Glu Leu Gln Ala Leu Lys Lys Glu Leu Ala Gln
            20                  25

<210> SEQ ID NO 5
<211> LENGTH: 30
<212> TYPE: PRT
<213> ORGANISM: Artificial Sequence
<220> FEATURE:
<223> OTHER INFORMATION: artificial peptide

<400> SEQUENCE: 5

Glu Gln Leu Glu Lys Lys Leu Gln Ala Leu Glu Lys Lys Leu Ala Gln
1               5                   10                  15
```

```
Leu Glu Trp Lys Asn Gln Ala Leu Glu Lys Lys Leu Ala Gln
            20              25              30

<210> SEQ ID NO 6
<211> LENGTH: 40
<212> TYPE: PRT
<213> ORGANISM: Artificial Sequence
<220> FEATURE:
<223> OTHER INFORMATION: artificial peptide

<400> SEQUENCE: 6

Glu Gln Leu Glu Lys Lys Leu Gln Ala Leu Glu Lys Lys Leu Ala Gln
1               5               10              15

Leu Glu Trp Lys Asn Gln Ala Leu Glu Lys Lys Leu Ala Gln Gly Gly
            20              25              30

Gly Gly Ser Gly Gly Gly Gly Ser
        35              40

<210> SEQ ID NO 7
<211> LENGTH: 39
<212> TYPE: PRT
<213> ORGANISM: Artificial Sequence
<220> FEATURE:
<223> OTHER INFORMATION: artificial peptide

<400> SEQUENCE: 7

Gly Gly Gly Gly Ser Gly Gly Gly Gly Ser Ala Leu Lys Lys Glu Leu
1               5               10              15

Gln Ala Asn Lys Lys Glu Leu Ala Gln Leu Lys Trp Glu Leu Gln Ala
            20              25              30

Leu Lys Lys Glu Leu Ala Gln
        35

<210> SEQ ID NO 8
<211> LENGTH: 5
<212> TYPE: PRT
<213> ORGANISM: Artificial Sequence
<220> FEATURE:
<223> OTHER INFORMATION: artificial peptide

<400> SEQUENCE: 8

Gly Gly Pro Gly Gly
1               5

<210> SEQ ID NO 9
<211> LENGTH: 5
<212> TYPE: PRT
<213> ORGANISM: Artificial Sequence
<220> FEATURE:
<223> OTHER INFORMATION: artificial peptide

<400> SEQUENCE: 9

Gly Pro Gly Gly Gly
1               5

<210> SEQ ID NO 10
<211> LENGTH: 11
<212> TYPE: PRT
<213> ORGANISM: Artificial Sequence
<220> FEATURE:
<223> OTHER INFORMATION: artificial peptide

<400> SEQUENCE: 10

Gly Gly Gly Gly Ser Gly Gly Gly Gly Gly Ser
```

-continued

```
1               5                   10

<210> SEQ ID NO 11
<211> LENGTH: 5
<212> TYPE: PRT
<213> ORGANISM: Artificial Sequence
<220> FEATURE:
<223> OTHER INFORMATION: artificial peptide

<400> SEQUENCE: 11

Gly Gly Gly Gly Ser
1               5

<210> SEQ ID NO 12
<211> LENGTH: 10
<212> TYPE: PRT
<213> ORGANISM: Artificial Sequence
<220> FEATURE:
<223> OTHER INFORMATION: artificial peptide

<400> SEQUENCE: 12

Gly Gly Gly Gly Ser Gly Gly Gly Gly Ser
1               5                   10

<210> SEQ ID NO 13
<211> LENGTH: 15
<212> TYPE: PRT
<213> ORGANISM: Artificial Sequence
<220> FEATURE:
<223> OTHER INFORMATION: artificial peptide

<400> SEQUENCE: 13

Gly Gly Gly Gly Ser Gly Gly Gly Gly Ser Gly Gly Gly Gly Ser
1               5                   10                  15

<210> SEQ ID NO 14
<211> LENGTH: 20
<212> TYPE: PRT
<213> ORGANISM: Artificial Sequence
<220> FEATURE:
<223> OTHER INFORMATION: artificial peptide)

<400> SEQUENCE: 14

Gly Gly Gly Gly Ser Gly Gly Gly Gly Ser Gly Gly Gly Gly Ser Gly
1               5                   10                  15

Gly Gly Gly Ser
            20

<210> SEQ ID NO 15
<211> LENGTH: 90
<212> TYPE: PRT
<213> ORGANISM: Artificial Sequence
<220> FEATURE:
<223> OTHER INFORMATION: artificial peptide

<400> SEQUENCE: 15

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
            35                  40                  45

Cys Glu Pro Gly Gly Gly Gly Ser Gly Gly Gly Gly Ser Ala Leu Lys
        50                  55                  60
```

-continued

```
Lys Glu Leu Gln Ala Asn Lys Lys Glu Leu Ala Gln Leu Lys Trp Glu
65                  70                  75                  80

Leu Gln Ala Leu Lys Lys Glu Leu Ala Gln
                85                  90

<210> SEQ ID NO 16
<211> LENGTH: 361
<212> TYPE: PRT
<213> ORGANISM: Artificial Sequence
<220> FEATURE:
<223> OTHER INFORMATION: artificial peptide

<400> SEQUENCE: 16

Gln Leu Glu Lys Lys Leu Gln Ala Leu Glu Lys Lys Leu Ala Gln Leu
1               5                   10                  15

Glu Trp Lys Asn Gln Ala Leu Glu Lys Lys Leu Ala Gln Gly Gly Gly
            20                  25                  30

Gly Ser Gly Gly Gly Gly Ser Lys Cys Val Glu Glu Leu Pro Glu Trp
        35                  40                  45

Asn Phe Asp Gly Ser Ser Thr Phe Gln Ser Glu Gly Ser Asn Ser Asp
    50                  55                  60

Met Tyr Leu His Pro Val Ala Met Phe Arg Asp Pro Phe Arg Lys Asp
65                  70                  75                  80

Pro Asn Lys Leu Val Leu Cys Glu Val Phe Lys Tyr Asn Arg Lys Pro
                85                  90                  95

Ala Glu Thr Asn Leu Arg His Ile Cys Lys Arg Ile Met Asp Met Val
            100                 105                 110

Ser Asn Gln His Pro Trp Phe Gly Met Glu Gln Glu Tyr Thr Leu Met
            115                 120                 125

Gly Thr Asp Gly His Pro Phe Gly Trp Pro Ser Asn Gly Phe Pro Gly
    130                 135                 140

Pro Gln Gly Pro Tyr Tyr Cys Gly Val Gly Ala Asp Lys Ala Tyr Gly
145                 150                 155                 160

Arg Asp Ile Val Glu Ala His Tyr Arg Ala Cys Leu Tyr Ala Gly Val
            165                 170                 175

Lys Ile Thr Gly Thr Asn Ala Glu Val Met Pro Ala Gln Trp Glu Phe
            180                 185                 190

Gln Ile Gly Pro Cys Glu Gly Ile Arg Met Gly Asp His Leu Trp Ile
            195                 200                 205

Ala Arg Phe Ile Leu His Arg Val Cys Glu Asp Phe Gly Val Ile Ala
    210                 215                 220

Thr Phe Asp Pro Lys Pro Ile Pro Gly Asn Trp Asn Gly Ala Gly Cys
225                 230                 235                 240

His Thr Asn Phe Ser Thr Lys Ala Met Arg Glu Glu Asn Gly Leu Lys
            245                 250                 255

Cys Ile Glu Glu Ala Ile Asp Lys Leu Ser Lys Arg His Gln Tyr His
            260                 265                 270

Ile Arg Ala Tyr Asp Pro Lys Gly Gly Leu Asp Asn Ala Arg Arg Leu
            275                 280                 285

Thr Gly Phe His Glu Thr Ser Asn Ile Asn Asp Phe Ser Ala Gly Val
    290                 295                 300

Ala Asn Arg Gly Ala Ser Ile Arg Ile Pro Arg Thr Val Gly Gln Glu
305                 310                 315                 320

Lys Lys Gly Tyr Phe Glu Asp Arg Arg Pro Ser Ala Asn Cys Asp Pro
                325                 330                 335
```

-continued

```
Tyr Ala Val Thr Glu Ala Ile Val Arg Thr Cys Leu Leu Asn Glu Thr
        340                 345                 350

Gly Asp Glu Pro Phe Gln Tyr Lys Asn
        355                 360

<210> SEQ ID NO 17
<211> LENGTH: 91
<212> TYPE: PRT
<213> ORGANISM: Artificial Sequence
<220> FEATURE:
<223> OTHER INFORMATION: artificial peptide

<400> SEQUENCE: 17

Met Ala Thr Ser Ala Ser Ser His Leu Asn Lys Gly Ile Lys Gln Met
1                   5                   10                  15

Tyr Met Ser Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
        35                  40                  45

Cys Glu Pro Lys Gly Gly Gly Ser Gly Gly Gly Gly Ser Ala Leu
    50                  55                  60

Lys Lys Glu Leu Gln Ala Asn Lys Lys Glu Leu Ala Gln Leu Lys Trp
65                  70                  75                  80

Glu Leu Gln Ala Leu Lys Lys Glu Leu Ala Gln
                85                  90

<210> SEQ ID NO 18
<211> LENGTH: 361
<212> TYPE: PRT
<213> ORGANISM: Artificial Sequence
<220> FEATURE:
<223> OTHER INFORMATION: artificial peptide

<400> SEQUENCE: 18

Glu Gln Leu Glu Lys Lys Leu Gln Ala Leu Glu Lys Lys Leu Ala Gln
1                   5                   10                  15

Leu Glu Trp Lys Asn Gln Ala Leu Glu Lys Lys Leu Ala Gln Gly Gly
            20                  25                  30

Gly Gly Ser Gly Gly Gly Gly Ser Cys Val Glu Glu Leu Pro Glu Trp
        35                  40                  45

Asn Phe Asp Gly Ser Ser Thr Phe Gln Ser Glu Gly Ser Asn Ser Asp
    50                  55                  60

Met Tyr Leu His Pro Val Ala Met Phe Arg Asp Pro Phe Arg Lys Asp
65                  70                  75                  80

Pro Asn Lys Leu Val Leu Cys Glu Val Phe Lys Tyr Asn Arg Lys Pro
                85                  90                  95

Ala Glu Thr Asn Leu Arg His Ile Cys Lys Arg Ile Met Asp Met Val
            100                 105                 110

Ser Asn Gln His Pro Trp Phe Gly Met Glu Gln Glu Tyr Thr Leu Met
        115                 120                 125

Gly Thr Asp Gly His Pro Phe Gly Trp Pro Ser Asn Gly Phe Pro Gly
        130                 135                 140

Pro Gln Gly Pro Tyr Tyr Cys Gly Val Gly Ala Asp Lys Ala Tyr Gly
145                 150                 155                 160

Arg Asp Ile Val Glu Ala His Tyr Arg Ala Cys Leu Tyr Ala Gly Val
                165                 170                 175

Lys Ile Thr Gly Thr Asn Ala Glu Val Met Pro Ala Gln Trp Glu Phe
            180                 185                 190
```

-continued

```
Gln Ile Gly Pro Cys Glu Gly Ile Arg Met Gly Asp His Leu Trp Ile
        195                 200                 205

Ala Arg Phe Ile Leu His Arg Val Cys Glu Asp Phe Gly Val Ile Ala
    210                 215                 220

Thr Phe Asp Pro Lys Pro Ile Pro Gly Asn Trp Asn Gly Ala Gly Cys
225                 230                 235                 240

His Thr Asn Phe Ser Thr Lys Ala Met Arg Glu Glu Asn Gly Leu Lys
                245                 250                 255

Cys Ile Glu Glu Ala Ile Asp Lys Leu Ser Lys Arg His Gln Tyr His
            260                 265                 270

Ile Arg Ala Tyr Asp Pro Lys Gly Gly Leu Asp Asn Ala Arg Arg Leu
        275                 280                 285

Thr Gly Phe His Glu Thr Ser Asn Ile Asn Asp Phe Ser Ala Gly Val
    290                 295                 300

Ala Asn Arg Gly Ala Ser Ile Arg Ile Pro Arg Thr Val Gly Gln Glu
305                 310                 315                 320

Lys Lys Gly Tyr Phe Glu Asp Arg Arg Pro Ser Ala Asn Cys Asp Pro
                325                 330                 335

Tyr Ala Val Thr Glu Ala Ile Val Arg Thr Cys Leu Leu Asn Glu Thr
            340                 345                 350

Gly Asp Glu Pro Phe Gln Tyr Lys Asn
        355                 360

<210> SEQ ID NO 19
<211> LENGTH: 93
<212> TYPE: PRT
<213> ORGANISM: Artificial Sequence
<220> FEATURE:
<223> OTHER INFORMATION: artificial peptide

<400> SEQUENCE: 19

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
        35                  40                  45

Cys Glu Pro Lys Cys Val Gly Gly Gly Ser Gly Gly Gly Gly Ser
    50                  55                  60

Ala Leu Lys Lys Glu Leu Gln Ala Asn Lys Lys Glu Leu Ala Gln Leu
65                  70                  75                  80

Lys Trp Glu Leu Gln Ala Leu Lys Lys Glu Leu Ala Gln
                85                  90

<210> SEQ ID NO 20
<211> LENGTH: 359
<212> TYPE: PRT
<213> ORGANISM: Artificial Sequence
<220> FEATURE:
<223> OTHER INFORMATION: artificial peptide

<400> SEQUENCE: 20

Glu Gln Leu Glu Lys Lys Leu Gln Ala Leu Glu Lys Lys Leu Ala Gln
1               5                   10                  15

Leu Glu Trp Lys Asn Gln Ala Leu Glu Lys Lys Leu Ala Gln Gly Gly
            20                  25                  30

Gly Gly Ser Gly Gly Gly Gly Ser Glu Glu Leu Pro Glu Trp Asn Phe
```

-continued

```
              35                  40                  45

Asp Gly Ser Ser Thr Phe Gln Ser Glu Gly Ser Asn Ser Asp Met Tyr
    50                  55                  60

Leu His Pro Val Ala Met Phe Arg Asp Pro Phe Arg Lys Asp Pro Asn
65                  70                  75                  80

Lys Leu Val Leu Cys Glu Val Phe Lys Tyr Asn Arg Lys Pro Ala Glu
                85                  90                  95

Thr Asn Leu Arg His Ile Cys Lys Arg Ile Met Asp Met Val Ser Asn
            100                 105                 110

Gln His Pro Trp Phe Gly Met Glu Gln Glu Tyr Thr Leu Met Gly Thr
            115                 120                 125

Asp Gly His Pro Phe Gly Trp Pro Ser Asn Gly Phe Pro Gly Pro Gln
    130                 135                 140

Gly Pro Tyr Tyr Cys Gly Val Gly Ala Asp Lys Ala Tyr Gly Arg Asp
145                 150                 155                 160

Ile Val Glu Ala His Tyr Arg Ala Cys Leu Tyr Ala Gly Val Lys Ile
            165                 170                 175

Thr Gly Thr Asn Ala Glu Val Met Pro Ala Gln Trp Glu Phe Gln Ile
            180                 185                 190

Gly Pro Cys Glu Gly Ile Arg Met Gly Asp His Leu Trp Ile Ala Arg
            195                 200                 205

Phe Ile Leu His Arg Val Cys Glu Asp Phe Gly Val Ile Ala Thr Phe
    210                 215                 220

Asp Pro Lys Pro Ile Pro Gly Asn Trp Asn Gly Ala Gly Cys His Thr
225                 230                 235                 240

Asn Phe Ser Thr Lys Ala Met Arg Glu Glu Asn Gly Leu Lys Cys Ile
                245                 250                 255

Glu Glu Ala Ile Asp Lys Leu Ser Lys Arg His Gln Tyr His Ile Arg
            260                 265                 270

Ala Tyr Asp Pro Lys Gly Gly Leu Asp Asn Ala Arg Arg Leu Thr Gly
            275                 280                 285

Phe His Glu Thr Ser Asn Ile Asn Asp Phe Ser Ala Gly Val Ala Asn
    290                 295                 300

Arg Gly Ala Ser Ile Arg Ile Pro Arg Thr Val Gly Gln Glu Lys Lys
305                 310                 315                 320

Gly Tyr Phe Glu Asp Arg Arg Pro Ser Ala Asn Cys Asp Pro Tyr Ala
            325                 330                 335

Val Thr Glu Ala Ile Val Arg Thr Cys Leu Leu Asn Glu Thr Gly Asp
            340                 345                 350

Glu Pro Phe Gln Tyr Lys Asn
            355
```

```
<210> SEQ ID NO 21
<211> LENGTH: 94
<212> TYPE: PRT
<213> ORGANISM: Artificial Sequence
<220> FEATURE:
<223> OTHER INFORMATION: artificial peptide

<400> SEQUENCE: 21

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
                20                  25                  30

Val Asp Gly Thr Gly Glu Gly Leu Arg Cys Lys Thr Arg Thr Leu Asp
```

-continued

```
              35                 40                 45

Cys Glu Pro Lys Cys Val Glu Gly Gly Gly Gly Ser Gly Gly Gly Gly
    50                 55                 60

Ser Ala Leu Lys Lys Glu Leu Gln Ala Asn Lys Lys Glu Leu Ala Gln
65                 70                 75                 80

Leu Lys Trp Glu Leu Gln Ala Leu Lys Lys Glu Leu Ala Gln
                85                 90

<210> SEQ ID NO 22
<211> LENGTH: 358
<212> TYPE: PRT
<213> ORGANISM: Artificial Sequence
<220> FEATURE:
<223> OTHER INFORMATION: artificial peptide

<400> SEQUENCE: 22

Glu Gln Leu Glu Lys Lys Leu Gln Ala Leu Glu Lys Lys Leu Ala Gln
1               5                 10                 15

Leu Glu Trp Lys Asn Gln Ala Leu Glu Lys Lys Leu Ala Gln Gly Gly
                20                 25                 30

Gly Gly Ser Gly Gly Gly Gly Ser Glu Leu Pro Glu Trp Asn Phe Asp
          35                 40                 45

Gly Ser Ser Thr Phe Gln Ser Glu Gly Ser Asn Ser Asp Met Tyr Leu
    50                 55                 60

His Pro Val Ala Met Phe Arg Asp Pro Phe Arg Lys Asp Pro Asn Lys
65                 70                 75                 80

Leu Val Leu Cys Glu Val Phe Lys Tyr Asn Arg Lys Pro Ala Glu Thr
                85                 90                 95

Asn Leu Arg His Ile Cys Lys Arg Ile Met Asp Met Val Ser Asn Gln
            100                105                110

His Pro Trp Phe Gly Met Glu Gln Glu Tyr Thr Leu Met Gly Thr Asp
          115                120                125

Gly His Pro Phe Gly Trp Pro Ser Asn Gly Phe Pro Gly Pro Gln Gly
      130                135                140

Pro Tyr Tyr Cys Gly Val Gly Ala Asp Lys Ala Tyr Gly Arg Asp Ile
145                150                155                160

Val Glu Ala His Tyr Arg Ala Cys Leu Tyr Ala Gly Val Lys Ile Thr
              165                170                175

Gly Thr Asn Ala Glu Val Met Pro Ala Gln Trp Glu Phe Gln Ile Gly
            180                185                190

Pro Cys Glu Gly Ile Arg Met Gly Asp His Leu Trp Ile Ala Arg Phe
          195                200                205

Ile Leu His Arg Val Cys Glu Asp Phe Gly Val Ile Ala Thr Phe Asp
      210                215                220

Pro Lys Pro Ile Pro Gly Asn Trp Asn Gly Ala Gly Cys His Thr Asn
225                230                235                240

Phe Ser Thr Lys Ala Met Arg Glu Glu Asn Gly Leu Lys Cys Ile Glu
              245                250                255

Glu Ala Ile Asp Lys Leu Ser Lys Arg His Gln Tyr His Ile Arg Ala
            260                265                270

Tyr Asp Pro Lys Gly Gly Leu Asp Asn Ala Arg Arg Leu Thr Gly Phe
          275                280                285

His Glu Thr Ser Asn Ile Asn Asp Phe Ser Ala Gly Val Ala Asn Arg
      290                295                300

Gly Ala Ser Ile Arg Ile Pro Arg Thr Val Gly Gln Glu Lys Lys Gly
```

-continued

```
305                 310                 315                 320
Tyr Phe Glu Asp Arg Arg Pro Ser Ala Asn Cys Asp Pro Tyr Ala Val
                325                 330                 335

Thr Glu Ala Ile Val Arg Thr Cys Leu Leu Asn Glu Thr Gly Asp Glu
                340                 345                 350

Pro Phe Gln Tyr Lys Asn
            355

<210> SEQ ID NO 23
<211> LENGTH: 130
<212> TYPE: PRT
<213> ORGANISM: Artificial Sequence
<220> FEATURE:
<223> OTHER INFORMATION: artificial peptide

<400> SEQUENCE: 23

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
                20                  25                  30

Val Asp Gly Thr Gly Glu Gly Leu Arg Cys Lys Thr Arg Thr Leu Asp
            35                  40                  45

Cys Glu Pro Lys Cys Val Glu Glu Leu Pro Glu Trp Asn Phe Asp Gly
        50                  55                  60

Ser Ser Thr Phe Gln Ser Glu Gly Ser Asn Ser Asp Met Tyr Leu His
65                  70                  75                  80

Pro Val Ala Met Phe Arg Asp Pro Phe Arg Lys Gly Gly Gly Gly Ser
                85                  90                  95

Gly Gly Gly Gly Ser Ala Leu Lys Lys Glu Leu Gln Ala Asn Lys Lys
            100                 105                 110

Glu Leu Ala Gln Leu Lys Trp Glu Leu Gln Ala Leu Lys Lys Glu Leu
        115                 120                 125

Ala Gln
    130

<210> SEQ ID NO 24
<211> LENGTH: 322
<212> TYPE: PRT
<213> ORGANISM: Artificial Sequence
<220> FEATURE:
<223> OTHER INFORMATION: artificial peptide

<400> SEQUENCE: 24

Glu Gln Leu Glu Lys Lys Leu Gln Ala Leu Glu Lys Lys Leu Ala Gln
1               5                   10                  15

Leu Glu Trp Lys Asn Gln Ala Leu Glu Lys Lys Leu Ala Gln Gly Gly
                20                  25                  30

Gly Gly Ser Gly Gly Gly Gly Ser Asp Pro Asn Lys Leu Val Leu Cys
            35                  40                  45

Glu Val Phe Lys Tyr Asn Arg Lys Pro Ala Glu Thr Asn Leu Arg His
        50                  55                  60

Ile Cys Lys Arg Ile Met Asp Met Val Ser Asn Gln His Pro Trp Phe
65                  70                  75                  80

Gly Met Glu Gln Glu Tyr Thr Leu Met Gly Thr Asp Gly His Pro Phe
                85                  90                  95

Gly Trp Pro Ser Asn Gly Phe Pro Gly Pro Gln Gly Pro Tyr Tyr Cys
            100                 105                 110
```

```
Gly Val Gly Ala Asp Lys Ala Tyr Gly Arg Asp Ile Val Glu Ala His
        115                 120                 125

Tyr Arg Ala Cys Leu Tyr Ala Gly Val Lys Ile Thr Gly Thr Asn Ala
    130                 135                 140

Glu Val Met Pro Ala Gln Trp Glu Phe Gln Ile Gly Pro Cys Glu Gly
145                 150                 155                 160

Ile Arg Met Gly Asp His Leu Trp Ile Ala Arg Phe Ile Leu His Arg
                165                 170                 175

Val Cys Glu Asp Phe Gly Val Ile Ala Thr Phe Asp Pro Lys Pro Ile
            180                 185                 190

Pro Gly Asn Trp Asn Gly Ala Gly Cys His Thr Asn Phe Ser Thr Lys
            195                 200                 205

Ala Met Arg Glu Glu Asn Gly Leu Lys Cys Ile Glu Glu Ala Ile Asp
    210                 215                 220

Lys Leu Ser Lys Arg His Gln Tyr His Ile Arg Ala Tyr Asp Pro Lys
225                 230                 235                 240

Gly Gly Leu Asp Asn Ala Arg Arg Leu Thr Gly Phe His Glu Thr Ser
                245                 250                 255

Asn Ile Asn Asp Phe Ser Ala Gly Val Ala Asn Arg Gly Ala Ser Ile
                260                 265                 270

Arg Ile Pro Arg Thr Val Gly Gln Glu Lys Lys Gly Tyr Phe Glu Asp
        275                 280                 285

Arg Arg Pro Ser Ala Asn Cys Asp Pro Tyr Ala Val Thr Glu Ala Ile
    290                 295                 300

Val Arg Thr Cys Leu Leu Asn Glu Thr Gly Asp Glu Pro Phe Gln Tyr
305                 310                 315                 320

Lys Asn
```

```
<210> SEQ ID NO 25
<211> LENGTH: 131
<212> TYPE: PRT
<213> ORGANISM: Artificial Sequence
<220> FEATURE:
<223> OTHER INFORMATION: artificial peptide

<400> SEQUENCE: 25

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
                20                  25                  30

Val Asp Gly Thr Gly Glu Gly Leu Arg Cys Lys Thr Arg Thr Leu Asp
            35                  40                  45

Cys Glu Pro Lys Cys Val Glu Glu Leu Pro Glu Trp Asn Phe Asp Gly
        50                  55                  60

Ser Ser Thr Phe Gln Ser Glu Gly Ser Asn Ser Asp Met Tyr Leu His
65                  70                  75                  80

Pro Val Ala Met Phe Arg Asp Pro Phe Arg Lys Asp Gly Gly Gly Gly
                85                  90                  95

Ser Gly Gly Gly Gly Ser Ala Leu Lys Lys Glu Leu Gln Ala Asn Lys
                100                 105                 110

Lys Glu Leu Ala Gln Leu Lys Trp Glu Leu Gln Ala Leu Lys Lys Glu
        115                 120                 125

Leu Ala Gln
    130
```

```
<210> SEQ ID NO 26
<211> LENGTH: 321
<212> TYPE: PRT
<213> ORGANISM: Artificial Sequence
<220> FEATURE:
<223> OTHER INFORMATION: artificial peptide

<400> SEQUENCE: 26

Glu Gln Leu Glu Lys Lys Leu Gln Ala Leu Glu Lys Lys Leu Ala Gln
1               5                   10                  15

Leu Glu Trp Lys Asn Gln Ala Leu Glu Lys Lys Leu Ala Gln Gly Gly
                20                  25                  30

Gly Gly Ser Gly Gly Gly Gly Ser Pro Asn Lys Leu Val Leu Cys Glu
            35                  40                  45

Val Phe Lys Tyr Asn Arg Lys Pro Ala Glu Thr Asn Leu Arg His Ile
        50                  55                  60

Cys Lys Arg Ile Met Asp Met Val Ser Asn Gln His Pro Trp Phe Gly
65                  70                  75                  80

Met Glu Gln Glu Tyr Thr Leu Met Gly Thr Asp Gly His Pro Phe Gly
                85                  90                  95

Trp Pro Ser Asn Gly Phe Pro Gly Pro Gln Gly Pro Tyr Tyr Cys Gly
                100                 105                 110

Val Gly Ala Asp Lys Ala Tyr Gly Arg Asp Ile Val Glu Ala His Tyr
            115                 120                 125

Arg Ala Cys Leu Tyr Ala Gly Val Lys Ile Thr Gly Thr Asn Ala Glu
            130                 135                 140

Val Met Pro Ala Gln Trp Glu Phe Gln Ile Gly Pro Cys Glu Gly Ile
145                 150                 155                 160

Arg Met Gly Asp His Leu Trp Ile Ala Arg Phe Ile Leu His Arg Val
                165                 170                 175

Cys Glu Asp Phe Gly Val Ile Ala Thr Phe Asp Pro Lys Pro Ile Pro
                180                 185                 190

Gly Asn Trp Asn Gly Ala Gly Cys His Thr Asn Phe Ser Thr Lys Ala
            195                 200                 205

Met Arg Glu Glu Asn Gly Leu Lys Cys Ile Glu Glu Ala Ile Asp Lys
    210                 215                 220

Leu Ser Lys Arg His Gln Tyr His Ile Arg Ala Tyr Asp Pro Lys Gly
225                 230                 235                 240

Gly Leu Asp Asn Ala Arg Arg Leu Thr Gly Phe His Glu Thr Ser Asn
            245                 250                 255

Ile Asn Asp Phe Ser Ala Gly Val Ala Asn Arg Gly Ala Ser Ile Arg
            260                 265                 270

Ile Pro Arg Thr Val Gly Gln Glu Lys Lys Gly Tyr Phe Glu Asp Arg
            275                 280                 285

Arg Pro Ser Ala Asn Cys Asp Pro Tyr Ala Val Thr Glu Ala Ile Val
    290                 295                 300

Arg Thr Cys Leu Leu Asn Glu Thr Gly Asp Glu Pro Phe Gln Tyr Lys
305                 310                 315                 320

Asn

<210> SEQ ID NO 27
<211> LENGTH: 225
<212> TYPE: PRT
<213> ORGANISM: Artificial Sequence
<220> FEATURE:
<223> OTHER INFORMATION: artificial peptide
```

```
<400> SEQUENCE: 27

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
            35                  40                  45

Cys Glu Pro Lys Cys Val Glu Glu Leu Pro Glu Trp Asn Phe Asp Gly
        50                  55                  60

Ser Ser Thr Phe Gln Ser Glu Gly Ser Asn Ser Asp Met Tyr Leu His
65                  70                  75                  80

Pro Val Ala Met Phe Arg Asp Pro Phe Arg Lys Asp Pro Asn Lys Leu
                85                  90                  95

Val Leu Cys Glu Val Phe Lys Tyr Asn Arg Lys Pro Ala Glu Thr Asn
            100                 105                 110

Leu Arg His Ile Cys Lys Arg Ile Met Asp Met Val Ser Asn Gln His
        115                 120                 125

Pro Trp Phe Gly Met Glu Gln Glu Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Gly Gly Gly Ser Gly
            180                 185                 190

Gly Gly Gly Ser Ala Leu Lys Lys Glu Leu Gln Ala Asn Lys Lys Glu
        195                 200                 205

Leu Ala Gln Leu Lys Trp Glu Leu Gln Ala Leu Lys Lys Glu Leu Ala
    210                 215                 220

Gln
225

<210> SEQ ID NO 28
<211> LENGTH: 227
<212> TYPE: PRT
<213> ORGANISM: Artificial Sequence
<220> FEATURE:
<223> OTHER INFORMATION: artificial peptide

<400> SEQUENCE: 28

Glu Gln Leu Glu Lys Lys Leu Gln Ala Leu Glu Lys Lys Leu Ala Gln
1               5                   10                  15

Leu Glu Trp Lys Asn Gln Ala Leu Glu Lys Lys Leu Ala Gln Gly Gly
            20                  25                  30

Gly Gly Ser Gly Gly Gly Gly Ser Gly Val Lys Ile Thr Gly Thr Asn
        35                  40                  45

Ala Glu Val Met Pro Ala Gln Trp Glu Phe Gln Ile Gly Pro Cys Glu
        50                  55                  60

Gly Ile Arg Met Gly Asp His Leu Trp Ile Ala Arg Phe Ile Leu His
65                  70                  75                  80

Arg Val Cys Glu Asp Phe Gly Val Ile Ala Thr Phe Asp Pro Lys Pro
                85                  90                  95

Ile Pro Gly Asn Trp Asn Gly Ala Gly Cys His Thr Asn Phe Ser Thr
            100                 105                 110

Lys Ala Met Arg Glu Glu Asn Gly Leu Lys Cys Ile Glu Glu Ala Ile
```

-continued

```
                115              120              125

Asp Lys Leu Ser Lys Arg His Gln Tyr His Ile Arg Ala Tyr Asp Pro
    130              135              140

Lys Gly Gly Leu Asp Asn Ala Arg Arg Leu Thr Gly Phe His Glu Thr
145              150              155              160

Ser Asn Ile Asn Asp Phe Ser Ala Gly Val Ala Asn Arg Gly Ala Ser
                165              170              175

Ile Arg Ile Pro Arg Thr Val Gly Gln Glu Lys Lys Gly Tyr Phe Glu
            180              185              190

Asp Arg Arg Pro Ser Ala Asn Cys Asp Pro Tyr Ala Val Thr Glu Ala
            195              200              205

Ile Val Arg Thr Cys Leu Leu Asn Glu Thr Gly Asp Glu Pro Phe Gln
    210              215              220

Tyr Lys Asn
225
```

```
<210> SEQ ID NO 29
<211> LENGTH: 226
<212> TYPE: PRT
<213> ORGANISM: Artificial Sequence
<220> FEATURE:
<223> OTHER INFORMATION: artificial peptide

<400> SEQUENCE: 29

Met Ala Thr Ser Ala Ser Ser His Leu Asn Lys Gly Ile Lys Gln Met
1               5               10              15

Tyr Met Ser Leu Pro Gln Gly Glu Lys Val Gln Ala Met Tyr Ile Trp
            20              25              30

Val Asp Gly Thr Gly Glu Gly Leu Arg Cys Lys Thr Arg Thr Leu Asp
        35              40              45

Cys Glu Pro Lys Cys Val Glu Glu Leu Pro Glu Trp Asn Phe Asp Gly
    50              55              60

Ser Ser Thr Phe Gln Ser Glu Gly Ser Asn Ser Asp Met Tyr Leu His
65              70              75              80

Pro Val Ala Met Phe Arg Asp Pro Phe Arg Lys Asp Pro Asn Lys Leu
            85              90              95

Val Leu Cys Glu Val Phe Lys Tyr Asn Arg Lys Pro Ala Glu Thr Asn
            100             105             110

Leu Arg His Ile Cys Lys Arg Ile Met Asp Met Val Ser Asn Gln His
        115             120             125

Pro Trp Phe Gly Met Glu Gln Glu Tyr Thr Leu Met Gly Thr Asp Gly
    130             135             140

His Pro Phe Gly Trp Pro Ser Asn Gly Phe Pro Gly Pro Gln Gly Pro
145             150             155             160

Tyr Tyr Cys Gly Val Gly Ala Asp Lys Ala Tyr Gly Arg Asp Ile Val
            165             170             175

Glu Ala His Tyr Arg Ala Cys Leu Tyr Ala Gly Gly Gly Gly Gly Ser
            180             185             190

Gly Gly Gly Gly Ser Ala Leu Lys Lys Glu Leu Gln Ala Asn Lys Lys
            195             200             205

Glu Leu Ala Gln Leu Lys Trp Glu Leu Gln Ala Leu Lys Lys Glu Leu
    210             215             220

Ala Gln
225
```

```
<210> SEQ ID NO 30
<211> LENGTH: 226
<212> TYPE: PRT
<213> ORGANISM: Artificial Sequence
<220> FEATURE:
<223> OTHER INFORMATION: artificial peptide

<400> SEQUENCE: 30

Glu Gln Leu Glu Lys Lys Leu Gln Ala Leu Glu Lys Lys Leu Ala Gln
1               5                   10                  15

Leu Glu Trp Lys Asn Gln Ala Leu Glu Lys Lys Leu Ala Gln Gly Gly
            20                  25                  30

Gly Gly Ser Gly Gly Gly Gly Ser Val Lys Ile Thr Gly Thr Asn Ala
        35                  40                  45

Glu Val Met Pro Ala Gln Trp Glu Phe Gln Ile Gly Pro Cys Glu Gly
    50                  55                  60

Ile Arg Met Gly Asp His Leu Trp Ile Ala Arg Phe Ile Leu His Arg
65                  70                  75                  80

Val Cys Glu Asp Phe Gly Val Ile Ala Thr Phe Asp Pro Lys Pro Ile
                85                  90                  95

Pro Gly Asn Trp Asn Gly Ala Gly Cys His Thr Asn Phe Ser Thr Lys
            100                 105                 110

Ala Met Arg Glu Glu Asn Gly Leu Lys Cys Ile Glu Glu Ala Ile Asp
        115                 120                 125

Lys Leu Ser Lys Arg His Gln Tyr His Ile Arg Ala Tyr Asp Pro Lys
        130                 135                 140

Gly Gly Leu Asp Asn Ala Arg Arg Leu Thr Gly Phe His Glu Thr Ser
145                 150                 155                 160

Asn Ile Asn Asp Phe Ser Ala Gly Val Ala Asn Arg Gly Ala Ser Ile
                165                 170                 175

Arg Ile Pro Arg Thr Val Gly Gln Glu Lys Lys Gly Tyr Phe Glu Asp
            180                 185                 190

Arg Arg Pro Ser Ala Asn Cys Asp Pro Tyr Ala Val Thr Glu Ala Ile
            195                 200                 205

Val Arg Thr Cys Leu Leu Asn Glu Thr Gly Asp Glu Pro Phe Gln Tyr
    210                 215                 220

Lys Asn
225

<210> SEQ ID NO 31
<211> LENGTH: 283
<212> TYPE: PRT
<213> ORGANISM: Artificial Sequence
<220> FEATURE:
<223> OTHER INFORMATION: artificial peptide

<400> SEQUENCE: 31

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
        35                  40                  45

Cys Glu Pro Lys Cys Val Glu Glu Leu Pro Glu Trp Asn Phe Asp Gly
    50                  55                  60

Ser Ser Thr Phe Gln Ser Glu Gly Ser Asn Ser Asp Met Tyr Leu His
65                  70                  75                  80
```

-continued

```
Pro Val Ala Met Phe Arg Asp Pro Phe Arg Lys Asp Pro Asn Lys Leu
            85              90              95

Val Leu Cys Glu Val Phe Lys Tyr Asn Arg Lys Pro Ala Glu Thr Asn
            100             105             110

Leu Arg His Ile Cys Lys Arg Ile Met Asp Met Val Ser Asn Gln His
            115             120             125

Pro Trp Phe Gly Met Glu Gln Glu Tyr Thr Leu Met Gly Thr Asp Gly
    130             135             140

His Pro Phe Gly Trp Pro Ser Asn Gly Phe Pro Gly Pro Gln Gly Pro
145             150             155             160

Tyr Tyr Cys Gly Val Gly Ala Asp Lys Ala Tyr Gly Arg Asp Ile Val
            165             170             175

Glu Ala His Tyr Arg Ala Cys Leu Tyr Ala Gly Val Lys Ile Thr Gly
            180             185             190

Thr Asn Ala Glu Val Met Pro Ala Gln Trp Glu Phe Gln Ile Gly Pro
            195             200             205

Cys Glu Gly Ile Arg Met Gly Asp His Leu Trp Ile Ala Arg Phe Ile
    210             215             220

Leu His Arg Val Cys Glu Asp Phe Gly Val Ile Ala Thr Phe Asp Pro
225             230             235             240

Lys Pro Ile Pro Gly Gly Gly Gly Ser Gly Gly Gly Gly Ser Ala Leu
            245             250             255

Lys Lys Glu Leu Gln Ala Asn Lys Lys Glu Leu Ala Gln Leu Lys Trp
            260             265             270

Glu Leu Gln Ala Leu Lys Lys Glu Leu Ala Gln
            275             280
```

```
<210> SEQ ID NO 32
<211> LENGTH: 169
<212> TYPE: PRT
<213> ORGANISM: Artificial Sequence
<220> FEATURE:
<223> OTHER INFORMATION: artificial peptide

<400> SEQUENCE: 32

Glu Gln Leu Glu Lys Lys Leu Gln Ala Leu Glu Lys Lys Leu Ala Gln
1               5               10              15

Leu Glu Trp Lys Asn Gln Ala Leu Glu Lys Lys Leu Ala Gln Gly Gly
            20              25              30

Gly Gly Ser Gly Gly Gly Gly Ser Gly Asn Trp Asn Gly Ala Gly Cys
            35              40              45

His Thr Asn Phe Ser Thr Lys Ala Met Arg Glu Glu Asn Gly Leu Lys
    50              55              60

Cys Ile Glu Glu Ala Ile Asp Lys Leu Ser Lys Arg His Gln Tyr His
65              70              75              80

Ile Arg Ala Tyr Asp Pro Lys Gly Gly Leu Asp Asn Ala Arg Arg Leu
            85              90              95

Thr Gly Phe His Glu Thr Ser Asn Ile Asn Asp Phe Ser Ala Gly Val
            100             105             110

Ala Asn Arg Gly Ala Ser Ile Arg Ile Pro Arg Thr Val Gly Gln Glu
            115             120             125

Lys Lys Gly Tyr Phe Glu Asp Arg Arg Pro Ser Ala Asn Cys Asp Pro
            130             135             140

Tyr Ala Val Thr Glu Ala Ile Val Arg Thr Cys Leu Leu Asn Glu Thr
145             150             155             160
```

-continued

```
Gly Asp Glu Pro Phe Gln Tyr Lys Asn
            165

<210> SEQ ID NO 33
<211> LENGTH: 284
<212> TYPE: PRT
<213> ORGANISM: Artificial Sequence
<220> FEATURE:
<223> OTHER INFORMATION: artificial peptide

<400> SEQUENCE: 33

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
        35                  40                  45

Cys Glu Pro Lys Cys Val Glu Glu Leu Pro Glu Trp Asn Phe Asp Gly
    50                  55                  60

Ser Ser Thr Phe Gln Ser Glu Gly Ser Asn Ser Asp Met Tyr Leu His
65                  70                  75                  80

Pro Val Ala Met Phe Arg Asp Pro Phe Arg Lys Asp Pro Asn Lys Leu
                85                  90                  95

Val Leu Cys Glu Val Phe Lys Tyr Asn Arg Lys Pro Ala Glu Thr Asn
            100                 105                 110

Leu Arg His Ile Cys Lys Arg Ile Met Asp Met Val Ser Asn Gln His
        115                 120                 125

Pro Trp Phe Gly Met Glu Gln Glu Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
            180                 185                 190

Thr Asn Ala Glu Val Met Pro Ala Gln Trp Glu Phe Gln Ile Gly Pro
        195                 200                 205

Cys Glu Gly Ile Arg Met Gly Asp His Leu Trp Ile Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Gly Gly Gly Ser Gly Gly Gly Ser Ala
                245                 250                 255

Leu Lys Lys Glu Leu Gln Ala Asn Lys Lys Glu Leu Ala Gln Leu Lys
                260                 265                 270

Trp Glu Leu Gln Ala Leu Lys Lys Glu Leu Ala Gln
        275                 280

<210> SEQ ID NO 34
<211> LENGTH: 168
<212> TYPE: PRT
<213> ORGANISM: Artificial Sequence
<220> FEATURE:
<223> OTHER INFORMATION: artificial peptide

<400> SEQUENCE: 34

Glu Gln Leu Glu Lys Lys Leu Gln Ala Leu Glu Lys Lys Leu Ala Gln
1               5                   10                  15
```

Leu Glu Trp Lys Asn Gln Ala Leu Glu Lys Lys Leu Ala Gln Gly Gly
              20                  25                  30

Gly Gly Ser Gly Gly Gly Gly Ser Asn Trp Asn Gly Ala Gly Cys His
          35                  40                  45

Thr Asn Phe Ser Thr Lys Ala Met Arg Glu Glu Asn Gly Leu Lys Cys
          50                  55                  60

Ile Glu Glu Ala Ile Asp Lys Leu Ser Lys Arg His Gln Tyr His Ile
65                  70                  75                  80

Arg Ala Tyr Asp Pro Lys Gly Gly Leu Asp Asn Ala Arg Arg Leu Thr
                  85                  90                  95

Gly Phe His Glu Thr Ser Asn Ile Asn Asp Phe Ser Ala Gly Val Ala
              100                 105                 110

Asn Arg Gly Ala Ser Ile Arg Ile Pro Arg Thr Val Gly Gln Glu Lys
              115                 120                 125

Lys Gly Tyr Phe Glu Asp Arg Arg Pro Ser Ala Asn Cys Asp Pro Tyr
          130                 135                 140

Ala Val Thr Glu Ala Ile Val Arg Thr Cys Leu Leu Asn Glu Thr Gly
145                 150                 155                 160

Asp Glu Pro Phe Gln Tyr Lys Asn
                  165

<210> SEQ ID NO 35
<211> LENGTH: 381
<212> TYPE: PRT
<213> ORGANISM: Unknown
<220> FEATURE:
<223> OTHER INFORMATION: Canine species

<400> SEQUENCE: 35

Met Ala Thr Ser Ala Ser Ser His Leu Asn Lys Gly Ile Lys Gln Val
1               5                   10                  15

Tyr Met Ser Leu Pro Gln Gly Glu Lys Val Gln Ala Met Tyr Ile Trp
              20                  25                  30

Ile Asp Gly Thr Gly Glu Gly Leu Arg Cys Lys Thr Arg Thr Leu Asp
          35                  40                  45

Ser Glu Pro Lys Gly Val Glu Glu Leu Pro Glu Trp Asn Phe Asp Gly
          50                  55                  60

Ser Ser Thr Phe Gln Ser Glu Gly Ser Asn Ser Asp Met Tyr Leu Val
65                  70                  75                  80

Pro Ala Ala Met Phe Arg Asp Pro Phe Arg Lys Asp Pro Asn Lys Leu
                  85                  90                  95

Val Phe Cys Glu Val Phe Lys Tyr Asn Arg Lys Pro Ala Glu Thr Asn
              100                 105                 110

Leu Arg His Thr Cys Lys Arg Ile Met Asp Met Val Ser Asn Gln His
          115                 120                 125

Pro Trp Phe Gly Met Glu Gln Glu Tyr Thr Leu Met Gly Thr Asp Gly
          130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
              165                 170                 175

Glu Ala His Tyr Arg Ala Cys Leu Tyr Ala Gly Ile Lys Ile Ala Gly
              180                 185                 190

Thr Asn Ala Glu Val Met Pro Ala Gln Trp Glu Phe Gln Ile Gly Pro
          195                 200                 205

-continued

```
Cys Glu Gly Ile Asp Met Gly Asp His Leu Trp Val Ala Arg Phe Ile
    210             215                 220

Leu His Arg Val Cys Glu Asp Phe Gly Val Ile Ala Thr Phe Asp Pro
225             230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Tyr Ile Glu Glu
                260                 265                 270

Ser Ile Glu Lys Leu Ser Lys Arg His Gln Tyr His Ile Arg Ala Tyr
            275                 280                 285

Asp Pro Lys Gly Gly Leu Asp Asn Ala Arg Arg Leu Thr Gly Phe His
            290                 295                 300

Glu Thr Ser Asn Ile Asn Asp Phe Ser Ala Gly Val Ala Asn Arg Gly
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Phe Ser Val Thr
                340                 345                 350

Glu Ala Leu Ile Arg Thr Cys Leu Leu Asn Glu Thr Gly Asp Glu Pro
            355                 360                 365

Phe Gln Tyr Lys Asn Leu Glu His His His His His His
    370                 375                 380

<210> SEQ ID NO 36
<211> LENGTH: 373
<212> TYPE: PRT
<213> ORGANISM: Cricetulus griseus

<400> SEQUENCE: 36

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
            35                  40                  45

Cys Glu Pro Lys Cys Val Glu Glu Leu Pro Glu Trp Asn Phe Asp Gly
    50                  55                  60

Ser Ser Thr Phe Gln Ser Glu Ser Ser Asn Ser Asp Met Tyr Leu Ser
65                  70                  75                  80

Pro Val Ala Met Phe Arg Asp Pro Phe Arg Lys Glu Pro Asn Lys Leu
                85                  90                  95

Val Phe Cys Glu Val Phe Lys Tyr Asn Gln Lys Pro Ala Glu Thr Asn
                100                 105                 110

Leu Arg His Thr Cys Lys Arg Ile Met Asp Met Val Ser Asn Gln His
            115                 120                 125

Pro Trp Phe Gly Met Glu Gln Glu Tyr Thr Leu Leu Gly Thr Asp Gly
            130                 135                 140

His Pro Phe Gly Trp Pro Ser Asp Gly Phe Pro Gly Pro Gln Gly Leu
145                 150                 155                 160

Tyr Tyr Cys Gly Val Gly Ala Asp Lys Ala Tyr Arg Arg Asp Ile Met
                165                 170                 175

Glu Ala His Tyr Arg Ala Cys Leu Tyr Ala Gly Val Lys Ile Thr Gly
            180                 185                 190

Thr Tyr Ala Glu Val Lys His Ala Gln Trp Glu Phe Gln Ile Gly Pro
```

-continued

```
                195                 200                 205

Cys Glu Gly Ile Arg Met Gly Asp His Leu Trp Val Ala Arg Phe Ile
    210                 215                 220

Leu His Arg Val Cys Lys Asp Phe Gly Val Ile Ala Thr Phe Asp Ser
225                 230                 235                 240

Lys Pro Ile Pro Gly Asn Trp Asn Gly Ala Gly Cys His Thr Asn Phe
                245                 250                 255

Ser Thr Lys Thr Met Arg Glu Glu Asn Gly Leu Lys His Ile Lys Glu
                260                 265                 270

Ala Ile Glu Lys Leu Ser Lys Arg His Arg Tyr His Ile Arg Ala Tyr
                275                 280                 285

Asp Pro Lys Gly Gly Leu Asp Asn Ala Arg Arg Leu Thr Gly Phe His
                290                 295                 300

Lys Thr Ser Asn Ile Asn Asp Phe Ser Ala Gly Val Ala Asp Arg Ser
305                 310                 315                 320

Ala Ser Ile Arg Ile Pro Arg Thr Val Gly Gln Glu Lys Lys Gly Tyr
                325                 330                 335

Phe Glu Ala Arg Cys Pro Ser Ala Asn Cys Asp Pro Phe Ala Val Thr
                340                 345                 350

Glu Ala Ile Val Arg Thr Cys Leu Leu Asn Glu Thr Gly Asp Gln Pro
                355                 360                 365

Phe Gln Tyr Lys Asn
    370

<210> SEQ ID NO 37
<211> LENGTH: 373
<212> TYPE: PRT
<213> ORGANISM: Unknown
<220> FEATURE:
<223> OTHER INFORMATION: Unknown organism origin

<400> SEQUENCE: 37

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
                20                  25                  30

Val Asp Gly Thr Gly Glu Gly Leu Arg Cys Lys Thr Arg Thr Leu Asp
                35                  40                  45

Cys Glu Pro Lys Cys Val Glu Glu Leu Pro Glu Trp Asn Phe Asp Gly
    50                  55                  60

Ser Ser Thr Phe Gln Ser Glu Gly Ser Asn Ser Asp Met Tyr Leu His
65                  70                  75                  80

Pro Val Ala Met Phe Arg Asp Pro Phe Arg Lys Asp Pro Asn Lys Leu
                85                  90                  95

Val Leu Cys Glu Val Phe Lys Tyr Asn Arg Lys Pro Ala Glu Thr Asn
                100                 105                 110

Leu Arg His Ile Cys Lys Arg Ile Met Asp Met Val Ser Asn Gln His
                115                 120                 125

Pro Trp Phe Gly Met Glu Gln Glu Tyr Thr Leu Met Gly Thr Asp Gly
                130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
```

-continued

```
                    180                 185                 190

Thr Asn Ala Glu Val Met Pro Ala Gln Trp Glu Phe Gln Ile Gly Pro
        195                 200                 205

Cys Glu Gly Ile Arg Met Gly Asp His Leu Trp Ile Ala Arg Phe Ile
        210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Cys Ile Glu Glu
                260                 265                 270

Ala Ile Asp Lys Leu Ser Lys Arg His Gln Tyr His Ile Arg Ala Tyr
                275                 280                 285

Asp Pro Lys Gly Gly Leu Asp Asn Ala Arg Arg Leu Thr Gly Phe His
        290                 295                 300

Glu Thr Ser Asn Ile Asn Asp Phe Ser Ala Gly Val Ala Asn Arg Gly
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Tyr Ala Val Thr
                340                 345                 350

Glu Ala Ile Val Arg Thr Cys Leu Leu Asn Glu Thr Gly Asp Glu Pro
                355                 360                 365

Phe Gln Tyr Lys Asn
        370

<210> SEQ ID NO 38
<211> LENGTH: 373
<212> TYPE: PRT
<213> ORGANISM: Homo sapiens

<400> SEQUENCE: 38

Met Thr Thr Ser Ala Ser Ser His Leu Asn Lys Gly Ile Lys Gln Val
1               5                   10                  15

Tyr Met Ser Leu Pro Gln Gly Glu Lys Val Gln Ala Met Tyr Ile Trp
                20                  25                  30

Ile Asp Gly Thr Gly Glu Gly Leu Arg Cys Lys Thr Arg Thr Leu Asp
            35                  40                  45

Ser Glu Pro Lys Cys Val Glu Glu Leu Pro Glu Trp Asn Phe Asp Gly
        50                  55                  60

Ser Ser Thr Leu Gln Ser Glu Gly Ser Asn Ser Asp Met Tyr Leu Val
65                  70                  75                  80

Pro Ala Ala Met Phe Arg Asp Pro Phe Arg Lys Asp Pro Asn Lys Leu
                85                  90                  95

Val Leu Cys Glu Val Phe Lys Tyr Asn Arg Arg Pro Ala Glu Thr Asn
                100                 105                 110

Leu Arg His Thr Cys Lys Arg Ile Met Asp Met Val Ser Asn Gln His
                115                 120                 125

Pro Trp Phe Gly Met Glu Gln Glu Tyr Thr Leu Met Gly Thr Asp Gly
        130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Arg Ala Tyr Gly Arg Asp Ile Val
                165                 170                 175
```

-continued

```
Glu Ala His Tyr Arg Ala Cys Leu Tyr Ala Gly Val Lys Ile Ala Gly
            180                 185                 190

Thr Asn Ala Glu Val Met Pro Ala Gln Trp Glu Phe Gln Ile Gly Pro
            195                 200                 205

Cys Glu Gly Ile Ser Met Gly Asp His Leu Trp Val Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Tyr Ile Glu Glu
            260                 265                 270

Ala Ile Glu Lys Leu Ser Lys Arg His Gln Tyr His Ile Arg Ala Tyr
            275                 280                 285

Asp Pro Lys Gly Gly Leu Asp Asn Ala Arg Arg Leu Thr Gly Phe His
            290                 295                 300

Glu Thr Ser Asn Ile Asn Asp Phe Ser Gly Gly Val Ala Asn Arg Ser
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Phe Ser Val Thr
                340                 345                 350

Glu Ala Leu Ile Arg Thr Cys Leu Leu Asn Glu Thr Gly Asp Glu Pro
            355                 360                 365

Phe Gln Tyr Lys Asn
            370

<210> SEQ ID NO 39
<211> LENGTH: 373
<212> TYPE: PRT
<213> ORGANISM: Rattus norvegicus

<400> SEQUENCE: 39

Met Ala Thr Ser Ala Ser Ser His Leu Asn Lys Gly Ile Lys Gln Met
1               5                   10                  15

Tyr Met Asn Leu Pro Gln Gly Glu Lys Ile Gln Leu Met Tyr Ile Trp
            20                  25                  30

Val Asp Gly Thr Gly Glu Gly Leu Arg Cys Lys Thr Arg Thr Leu Asp
            35                  40                  45

Cys Asp Pro Lys Cys Val Glu Glu Leu Pro Glu Trp Asn Phe Asp Gly
    50                  55                  60

Ser Ser Thr Phe Gln Ser Glu Gly Ser Asp Ser Asp Met Tyr Leu His
65                  70                  75                  80

Pro Val Ala Met Phe Arg Asp Pro Phe Arg Arg Asp Pro Asn Lys Leu
                85                  90                  95

Val Phe Cys Glu Val Phe Lys Tyr Asn Arg Lys Pro Ala Glu Thr Asn
            100                 105                 110

Leu Arg His Ser Cys Lys Arg Ile Met Asp Met Val Ser Ser Gln His
            115                 120                 125

Pro Trp Phe Gly Met Glu Gln Glu Tyr Thr Leu Met Gly Thr Asp Gly
            130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175
```

```
Glu Ala His Tyr Arg Ala Cys Leu Tyr Ala Gly Ile Lys Ile Thr Gly
            180                 185             190

Thr Asn Ala Glu Val Met Pro Ala Gln Trp Glu Phe Gln Ile Gly Pro
            195                 200             205

Cys Glu Gly Ile Arg Met Gly Asp His Leu Trp Val Ala Arg Phe Ile
    210                 215             220

Leu His Arg Val Cys Glu Asp Phe Gly Val Ile Ala Thr Phe Asp Pro
225                 230             235                 240

Lys Pro Ile Pro Gly Asn Trp Asn Gly Ala Gly Cys His Thr Asn Phe
                245             250             255

Ser Thr Lys Ala Met Arg Glu Glu Asn Gly Leu Arg Cys Ile Glu Glu
            260             265             270

Ala Ile Asp Lys Leu Ser Lys Arg His Gln Tyr His Ile Arg Ala Tyr
    275             280             285

Asp Pro Lys Gly Gly Leu Asp Asn Ala Arg Arg Leu Thr Gly Phe His
    290             295             300

Glu Thr Ser Asn Ile Asn Asp Phe Ser Ala Gly Val Ala Asn Arg Ser
305             310             315                 320

Ala Ser Ile Arg Ile Pro Arg Ile Val Gly Gln Glu Lys Lys Gly Tyr
            325             330             335

Phe Glu Asp Arg Arg Pro Ser Ala Asn Cys Asp Pro Tyr Ala Val Thr
            340             345             350

Glu Ala Ile Val Arg Thr Cys Leu Leu Asn Glu Thr Gly Asp Glu Pro
            355             360             365

Phe Gln Tyr Lys Asn
    370
```